US009604068B2

(12) United States Patent
Malinowski

(10) Patent No.: US 9,604,068 B2
(45) Date of Patent: Mar. 28, 2017

(54) SYSTEMS AND METHODS FOR MAKING AND USING IMPROVED CONNECTOR CONTACTS FOR ELECTRICAL STIMULATION SYSTEMS

(71) Applicant: Boston Scientific Neuromodulation Corporation, Valencia, CA (US)

(72) Inventor: Zdzislaw Bernard Malinowski, Castaic, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 14/935,240

(22) Filed: Nov. 6, 2015

(65) Prior Publication Data
US 2016/0129265 A1 May 12, 2016

Related U.S. Application Data

(60) Provisional application No. 62/077,762, filed on Nov. 10, 2014.

(51) Int. Cl.
*A61N 1/37* (2006.01)
*A61N 1/375* (2006.01)
*A61N 1/05* (2006.01)

(52) U.S. Cl.
CPC .......... *A61N 1/3752* (2013.01); *A61N 1/056* (2013.01)

(58) Field of Classification Search
CPC ...... A61N 1/375; A61N 1/3752; A61N 1/056; A61N 1/3754; A61N 1/3756; A61N 1/3758
See application file for complete search history.

(56) References Cited

U.S. PATENT DOCUMENTS

| 4,602,624 | A | 7/1986 | Naples et al. |
| 4,630,611 | A | 12/1986 | King |
| 4,744,370 | A | 5/1988 | Harris |
| 5,000,194 | A | 3/1991 | van den Honert et al. |
| 5,135,001 | A | 8/1992 | Sinofsky et al. |

(Continued)

FOREIGN PATENT DOCUMENTS

| EP | 0580928 A1 | 2/1994 |
| EP | 0650694 B1 | 7/1998 |

(Continued)

*Primary Examiner* — Paula J Stice
(74) *Attorney, Agent, or Firm* — Lowe Graham Jones PLLC; Bruce E. Black

(57) ABSTRACT

A connector for an implantable electrical medical device includes a connector lumen defined in an elongated connector housing and adapted for receiving a portion of a lead. Connector-contact assemblies are disposed in the connector lumen. Each of the connector-contact assemblies includes a contact housing. Multiple connector contacts are arranged along perimeters of inner surfaces of the contact housings such that the connector contacts are not in electrical contact with one another. Each of the connector contacts includes a biasing structure that physically contacts terminals disposed along the lead when the lead is received by the connector lumen. For each connector contact of a particular connector-contact assembly, the biasing structure extends around no more than 70% of the perimeter of the inner surface of the contact housing and is circumferentially-offset from the biasing structures of the remaining connector contacts of the connector-contact assembly.

20 Claims, 13 Drawing Sheets

(56) References Cited

U.S. PATENT DOCUMENTS

| | | |
|---|---|---|
| 5,374,285 A | 12/1994 | Vaiani et al. |
| 5,458,629 A | 10/1995 | Baudino et al. |
| 5,522,874 A | 6/1996 | Gates |
| 5,711,316 A | 1/1998 | Elsberry et al. |
| 5,713,922 A | 2/1998 | King |
| 5,800,350 A | 9/1998 | Coppleson et al. |
| 5,843,148 A | 12/1998 | Gijsbers et al. |
| 5,938,688 A | 8/1999 | Schiff |
| 5,987,361 A | 11/1999 | Mortimer |
| 6,018,684 A | 1/2000 | Bartig et al. |
| 6,134,478 A | 10/2000 | Spehr |
| 6,161,047 A | 12/2000 | King et al. |
| 6,167,311 A | 12/2000 | Rezai |
| 6,181,969 B1 | 1/2001 | Gord |
| 6,322,559 B1 | 11/2001 | Daulton et al. |
| 6,510,347 B2 | 1/2003 | Borkan |
| 6,516,227 B1 | 2/2003 | Meadows et al. |
| 6,556,873 B1 | 4/2003 | Smits |
| 6,564,078 B1 | 5/2003 | Marino et al. |
| 6,609,029 B1 | 8/2003 | Mann et al. |
| 6,609,032 B1 | 8/2003 | Woods et al. |
| 6,678,564 B2 | 1/2004 | Ketterl et al. |
| 6,741,892 B1 | 5/2004 | Meadows et al. |
| 6,757,970 B1 | 7/2004 | Kuzma et al. |
| 7,027,852 B2 | 4/2006 | Helland |
| 7,047,084 B2 | 5/2006 | Erickson et al. |
| 7,203,548 B2 | 4/2007 | Whitehurst et al. |
| 7,244,150 B1 | 7/2007 | Brase et al. |
| 7,292,890 B2 | 11/2007 | Whitehurst et al. |
| 7,437,193 B2 | 10/2008 | Parramon et al. |
| 7,450,997 B1 | 11/2008 | Pianca et al. |
| 7,489,971 B1 | 2/2009 | Franz |
| 7,668,601 B2 | 2/2010 | Hegland et al. |
| 7,672,734 B2 | 3/2010 | Anderson et al. |
| 7,761,165 B1 | 7/2010 | He et al. |
| 7,761,985 B2 | 7/2010 | Hegland et al. |
| 7,783,359 B2 | 8/2010 | Meadows |
| 7,792,590 B1 | 9/2010 | Pianca et al. |
| 7,809,446 B2 | 10/2010 | Meadows |
| 7,822,482 B2 | 10/2010 | Gerber |
| 7,840,188 B2 | 11/2010 | Kurokawa |
| 7,848,802 B2 | 12/2010 | Goetz |
| 7,856,707 B2 | 12/2010 | Cole |
| 7,860,570 B2 | 12/2010 | Whitehurst et al. |
| 7,949,395 B2 | 5/2011 | Kuzma |
| 7,974,705 B2 | 7/2011 | Zdeblick et al. |
| 7,974,706 B2 | 7/2011 | Moffitt et al. |
| 7,979,140 B2 | 7/2011 | Schulman |
| 8,000,808 B2 | 8/2011 | Hegland et al. |
| 8,019,440 B2 | 9/2011 | Kokones et al. |
| 8,036,755 B2 | 10/2011 | Franz |
| 8,041,309 B2 | 10/2011 | Kurokawa |
| 8,099,177 B2 | 1/2012 | Dahlberg |
| 8,175,710 B2 | 5/2012 | He |
| 8,224,450 B2 | 7/2012 | Brase |
| 8,225,504 B2 | 7/2012 | Dye et al. |
| 8,271,094 B1 | 9/2012 | Moffitt et al. |
| 8,295,944 B2 | 10/2012 | Howard et al. |
| 8,321,025 B2 | 11/2012 | Bedenbaugh |
| 8,359,107 B2 | 1/2013 | Pianca et al. |
| 8,364,278 B2 | 1/2013 | Pianca et al. |
| 8,391,985 B2 | 3/2013 | McDonald |
| 8,583,237 B2 | 11/2013 | Bedenbaugh |
| 8,688,235 B1 | 4/2014 | Pianca et al. |
| 2001/0023368 A1 | 9/2001 | Black et al. |
| 2002/0156513 A1 | 10/2002 | Borkan |
| 2002/0183817 A1 | 12/2002 | Van Venrooij et al. |
| 2005/0015130 A1 | 1/2005 | Gill |
| 2005/0038489 A1 | 2/2005 | Grill |
| 2005/0171587 A1 | 8/2005 | Daglow et al. |
| 2006/0025841 A1 | 2/2006 | McIntyre |
| 2006/0247697 A1 | 11/2006 | Sharma et al. |
| 2007/0150036 A1 | 6/2007 | Anderson |
| 2007/0168007 A1 | 7/2007 | Kuzma et al. |
| 2007/0203546 A1 | 8/2007 | Stone et al. |
| 2007/0219551 A1 | 9/2007 | Honour et al. |
| 2008/0077186 A1 | 3/2008 | Thompson et al. |
| 2008/0103580 A1 | 5/2008 | Gerber |
| 2008/0114230 A1 | 5/2008 | Addis |
| 2008/0215125 A1 | 9/2008 | Farah et al. |
| 2008/0255647 A1 | 10/2008 | Jensen et al. |
| 2009/0054941 A1 | 2/2009 | Eggen et al. |
| 2009/0187222 A1 | 7/2009 | Barker |
| 2009/0204192 A1 | 8/2009 | Carlton et al. |
| 2009/0276021 A1 | 11/2009 | Meadows et al. |
| 2010/0030298 A1 | 2/2010 | Martens et al. |
| 2010/0036468 A1 | 2/2010 | Decre et al. |
| 2010/0076535 A1 | 3/2010 | Pianca et al. |
| 2010/0077606 A1 | 4/2010 | Black et al. |
| 2010/0082076 A1 | 4/2010 | Lee et al. |
| 2010/0094387 A1 | 4/2010 | Pianca et al. |
| 2010/0100152 A1 | 4/2010 | Martens et al. |
| 2010/0268298 A1 | 10/2010 | Moffitt et al. |
| 2010/0269338 A1 | 10/2010 | Dye |
| 2010/0269339 A1 | 10/2010 | Dye et al. |
| 2010/0287770 A1 | 11/2010 | Dadd et al. |
| 2011/0004267 A1 | 1/2011 | Meadows |
| 2011/0005069 A1 | 1/2011 | Pianca |
| 2011/0047795 A1 | 3/2011 | Turner et al. |
| 2011/0056076 A1 | 3/2011 | Hegland et al. |
| 2011/0077699 A1 | 3/2011 | Swanson et al. |
| 2011/0078900 A1 | 4/2011 | Pianca et al. |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0131808 A1 | 6/2011 | Gill |
| 2011/0238129 A1 | 9/2011 | Moffitt et al. |
| 2011/0245903 A1 | 10/2011 | Schulte et al. |
| 2011/0301665 A1 | 12/2011 | Mercanzini et al. |
| 2011/0313500 A1 | 12/2011 | Barker et al. |
| 2012/0016378 A1 | 1/2012 | Pianca et al. |
| 2012/0046710 A1 | 2/2012 | DiGiore et al. |
| 2012/0071949 A1 | 3/2012 | Pianca et al. |
| 2012/0165911 A1 | 6/2012 | Pianca |
| 2012/0197375 A1 | 8/2012 | Pianca et al. |
| 2012/0203316 A1 | 8/2012 | Moffitt et al. |
| 2012/0203320 A1 | 8/2012 | DiGiore et al. |
| 2012/0203321 A1 | 8/2012 | Moffitt et al. |
| 2012/0316615 A1 | 12/2012 | DiGiore et al. |
| 2013/0105071 A1 | 5/2013 | DiGiore et al. |
| 2013/0109254 A1 | 5/2013 | Klardie et al. |
| 2013/0197424 A1 | 8/2013 | Bedenbaugh |
| 2013/0197602 A1 | 8/2013 | Pianca et al. |
| 2013/0261684 A1 | 10/2013 | Howard |
| 2013/0317587 A1 | 11/2013 | Barker |
| 2013/0325091 A1 | 12/2013 | Pianca et al. |
| 2014/0039587 A1 | 2/2014 | Romero |
| 2014/0088666 A1 | 3/2014 | Goetz et al. |
| 2014/0142671 A1 | 5/2014 | Moffitt et al. |
| 2014/0180375 A1 | 6/2014 | Pianca et al. |
| 2014/0353001 A1 | 12/2014 | Romero et al. |
| 2014/0358207 A1 | 12/2014 | Romero |
| 2014/0358208 A1 | 12/2014 | Howard et al. |
| 2014/0358209 A1 | 12/2014 | Romero et al. |
| 2014/0358210 A1 | 12/2014 | Howard et al. |
| 2015/0018915 A1 | 1/2015 | Leven |
| 2015/0021817 A1 | 1/2015 | Romero et al. |
| 2015/0045864 A1 | 2/2015 | Howard |
| 2015/0066120 A1 | 3/2015 | Govea |
| 2015/0151113 A1 | 6/2015 | Govea et al. |

FOREIGN PATENT DOCUMENTS

| | | |
|---|---|---|
| EP | 0832667 B1 | 2/2004 |
| EP | 1181947 B1 | 1/2006 |
| EP | 2092952 A1 | 8/2009 |
| WO | 9732628 A1 | 9/1997 |
| WO | 9955411 A3 | 2/2000 |
| WO | 0038574 A1 | 7/2000 |
| WO | 2001058520 A1 | 8/2001 |
| WO | 02068042 A1 | 9/2002 |
| WO | 2004045707 A1 | 6/2004 |
| WO | 2008018067 A2 | 2/2008 |

(56) References Cited

FOREIGN PATENT DOCUMENTS

| | | |
|---|---|---|
| WO | 2008053789 A1 | 5/2008 |
| WO | 2008100841 | 8/2008 |
| WO | 2009025816 A1 | 2/2009 |
| WO | 2009102536 A1 | 8/2009 |
| WO | 2013162775 A2 | 10/2013 |
| WO | 2014018092 A1 | 1/2014 |

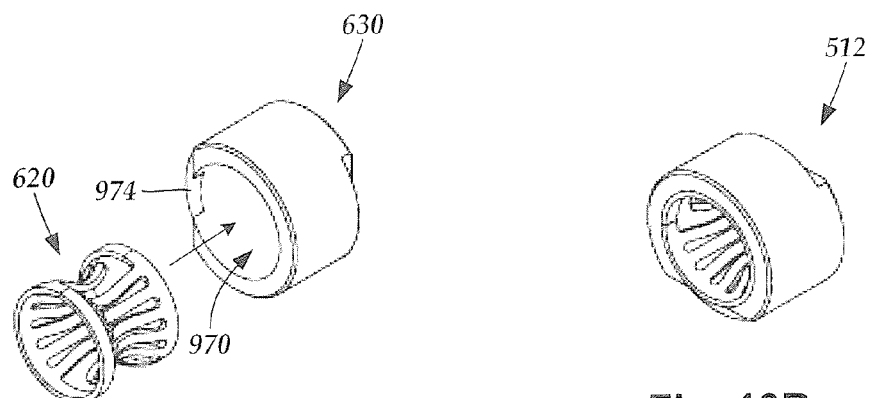
Fig. 10A
Fig. 10B
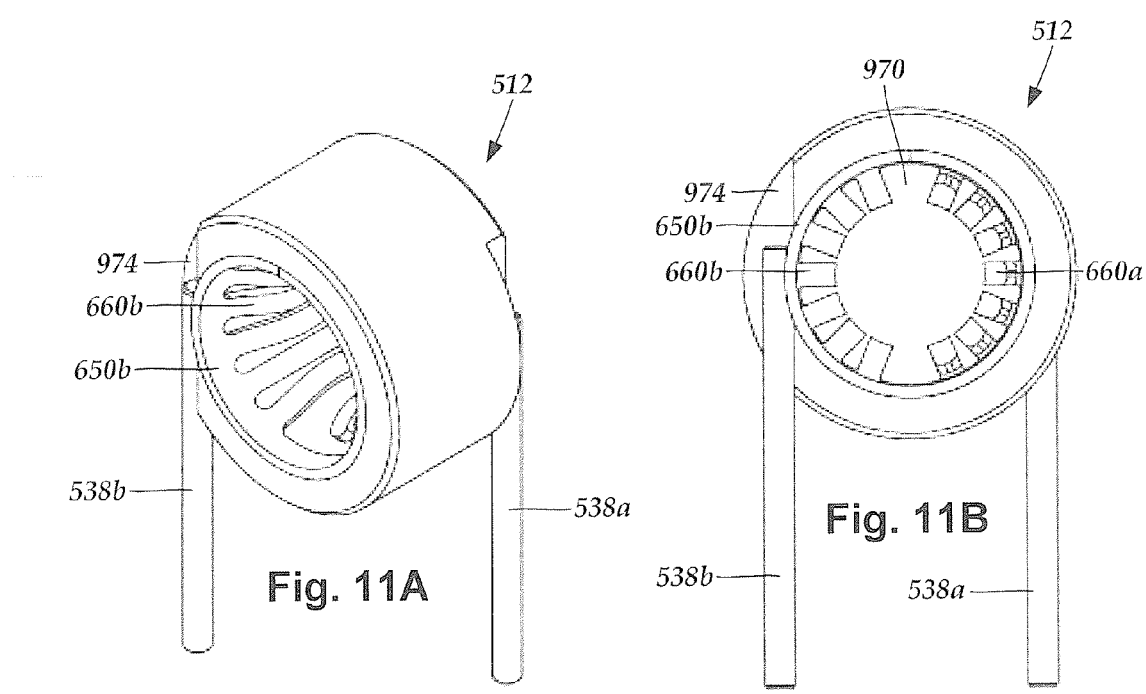
Fig. 11A
Fig. 11B

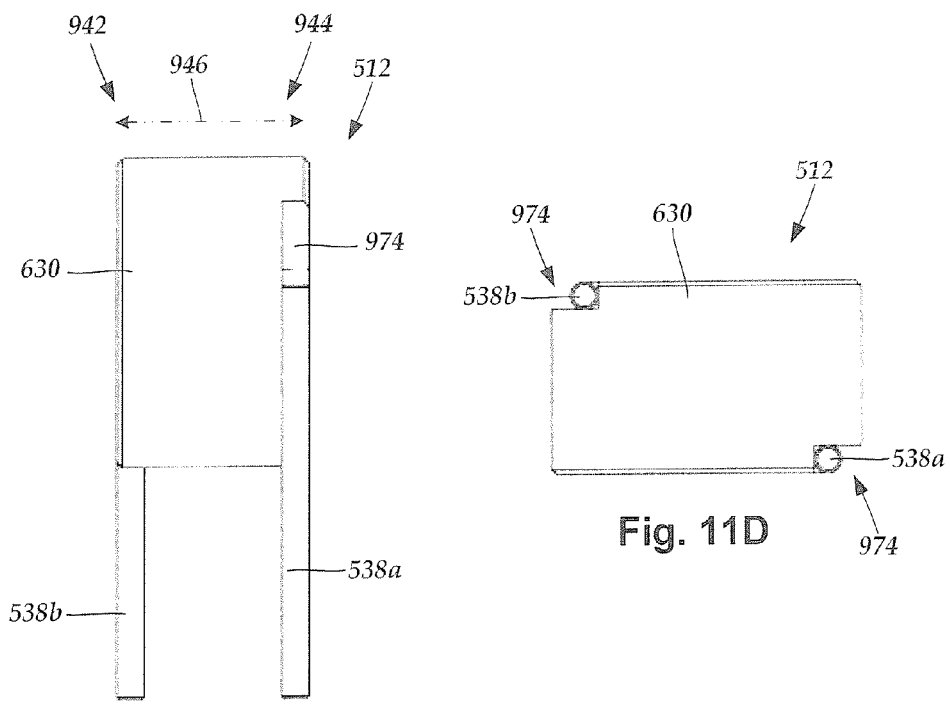
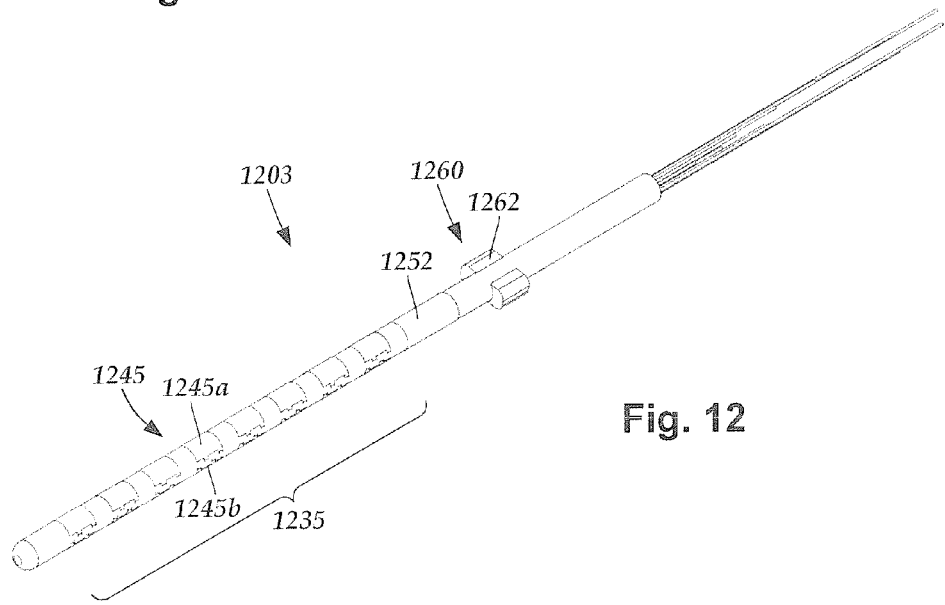

SYSTEMS AND METHODS FOR MAKING AND USING IMPROVED CONNECTOR CONTACTS FOR ELECTRICAL STIMULATION SYSTEMS

CROSS-REFERENCE TO RELATED APPLICATIONS

This application claims the benefit under 35 U.S.C. §119 (e) of U.S. Provisional Patent Application Ser. No. 62/077,762, filed Nov. 10, 2014, which is incorporated herein by reference.

FIELD

The present invention is directed to the area of implantable electrical stimulation systems and methods of making and using the systems. The present invention is also directed to implantable electrical stimulation systems having connectors with improved connector contacts, as well as methods of making and using the connectors, connector contacts, and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat incontinence, as well as a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

In one embodiment, a connector for an implantable electrical medical device includes an elongated connector housing having a first end and an opposing second end. A connector lumen is defined in the connector housing. The connector lumen is configured and arranged for receiving a lead or lead extension. Multiple connector-contact assemblies are disposed in the connector lumen. Each of the connector-contact assemblies includes a contact housing having a first end, an opposing second end, a longitudinal length, an inner surface, and an outer surface. The inner surface of the contact housing forms a perimeter of an open center portion defined by the contact housing. The open center portion has an inner diameter. Multiple connector contacts are arranged along the perimeter of the inner surface of the contact housing such that the connector contacts are not in electrical contact with one another. Each of the connector contacts includes a biasing structure configured and arranged to physically contact one of multiple terminals disposed along the lead or lead extension when the lead or lead extension is received by the connector lumen. For each of the connector contacts of the connector-contact assembly, the biasing structure extends around no more than 70% of the perimeter of the inner surface of the contact housing and is circumferentially-offset from the biasing structures of the remaining connector contacts of the connector-contact assembly along the perimeter of the inner surface of the contact housing. Multiple connector conductors are coupled to the connector-contact assemblies and extend along the connector housing.

In at least some embodiments, at least one of the connector-contact assemblies includes exactly two connector contacts. In at least some embodiments, each of the plurality of connector contacts includes exactly one biasing structure. In at least some embodiments, the biasing structure includes multiple biasing members. In at least some embodiments, for each of the connector contacts the biasing structure includes at least one bend that extends into the open center portion of the contact housing and that narrows the inner diameter of the open center portion.

In at least some embodiments, for each of the connector contacts the connector contact includes a base that is coupled to the biasing structure and that extends along at least 50% of the perimeter of the inner surface of the contact housing. In at least some embodiments, the base extends around the entire circumference of the open center region. In at least some embodiments, for each of the connector-contact assemblies the connector contacts include a first connector contact having a first base and a second connector contact having a second base, where the first connector contact and the second conductor contact are oriented in the contact housing with the first base disposed along the first end of the contact housing and the second base disposed along the second end of the contact housing.

In at least some embodiments, the contact housing is electrically nonconductive. In at least some embodiments, for at least one of the connector-contact assemblies the contact housing defines at least one connection region that extends through the contact housing from the outer surface to the inner surface and exposes a portion of at least one connector contact of the connector contacts disposed in the open center region of the contact housing to the outer surface of the contact housing. In at least some embodiments, for at least one of the connector-contact assemblies at least one of the connector contacts is aligned with the at least one connection region. In at least some embodiments, for at least one of the connector-contact assemblies the connection region includes a first connection region defined along the first end of the contact housing and a second connection region defined along the second end of the contact housing. In at least some embodiments, the first connection region and the second connection region are circumferentially-offset from one another along the perimeter of the inner surface of the contact housing.

In another embodiment, a lead extension includes a lead extension body and the above-described connector. The lead extension body has a proximal portion, a distal portion, a circumference, and a longitudinal length. The connector is disposed along the distal portion of the lead extension body. Lead extension terminals are disposed along the proximal portion of the lead extension body. Lead extension conductors electrically couple the connector contacts of the connector to the lead extension terminals.

In yet another embodiment, a lead assembly includes the above-described lead extension and a lead. The lead is configured and arranged for insertion into the connector lumen of the connector of the lead extension. The lead includes a lead body with a proximal portion, a distal portion, a circumference, and a longitudinal length. Lead electrodes are disposed along the distal portion of the lead body. Lead terminals are disposed along the proximal portion of the lead body. Lead conductors electrically couple the lead electrodes to the lead terminals.

In still yet another embodiment, a kit for an electrical stimulation system includes the above-described lead extension and a control module. The control module is coupleable to the proximal portion of the lead extension. The control module includes a housing and an electronic subassembly disposed in the housing.

In another embodiment, an electrical stimulation system includes the above-described kit and a lead. The lead is configured and arranged for insertion into the connector lumen of the connector of the control module of the kit. The lead includes a lead body with a proximal portion, a distal portion, a circumference, and a longitudinal length. Lead electrodes are disposed along the distal portion of the lead body. Lead terminals are disposed along the proximal portion of the lead body. Lead conductors electrically couple the lead electrodes to the lead terminals.

In yet another embodiment, a method of implanting an electrical stimulation system into a patient includes advancing the lead of the above-described electrical stimulation system into the patient; inserting the proximal portion of the lead into the connector lumen of the connector of the lead extension of the electrical stimulation system; and coupling the proximal portion of the lead extension to the control module of the electrical stimulation system.

In still yet another embodiment, a control module includes a sealed housing; an electronic subassembly disposed in the sealed housing; a header coupled to the sealed housing; and the above-described connector disposed in the header.

In another embodiment, an electrical stimulation system includes the above-described control module and a lead. The lead is configured and arranged for insertion into the connector lumen of the connector of the control module. The lead includes a lead body with a proximal portion, a distal portion, a circumference, and a longitudinal length. Lead electrodes are disposed along the distal portion of the lead body. Lead terminals are disposed along the proximal portion of the lead body. Lead conductors electrically couple the lead electrodes to the lead terminals.

In yet another embodiment, a method of implanting an electrical stimulation system into a patient includes advancing the above-described lead of the electrical stimulation system into the patient; and inserting the proximal portion of the lead into the connector lumen of the connector of the control module of the electrical stimulation system.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 10A is a schematic perspective view of one embodiment of the contact housing of FIG. 9A configured for receiving the connector-contact set of FIG. 8A, according to the invention;

FIG. 10B is a schematic perspective view of one embodiment of the connector-contact set of FIG. 8A disposed in the contact housing of FIG. 9A to form the connector-contact assembly of FIGS. 6A-6D, according to the invention;

FIG. 11A is a schematic perspective view of one embodiment of conductive members coupled to each individual connector contact of the connector-contact assembly of FIG. 10B, according to the invention;

FIG. 11B is a schematic end view of one embodiment of the conductive members of FIG. 11A coupled to each individual connector contact of the connector-contact assembly of FIG. 10B, according to the invention;

FIG. 11C is a schematic side view of one embodiment of the conductive members of FIG. 11A coupled to each individual connector contact of the connector-contact assembly of FIG. 10B, according to the invention;

FIG. 11D is a schematic bottom view of one embodiment of the conductive members of FIG. 11A coupled to each individual connector contact of the connector-contact assembly of FIG. 10B, according to the invention;

FIG. 12 is a schematic perspective view of one embodiment of a proximal portion of a lead suitable for insertion into the connector of FIG. 5, according to the invention;

DETAILED DESCRIPTION

The present invention is directed to the area of implantable electrical stimulation systems and methods of making and using the systems. The present invention is also directed to implantable electrical stimulation systems having connectors with improved connector contacts, as well as methods of making and using the connectors, connector contacts, and electrical stimulation systems.

Suitable implantable electrical stimulation systems include, but are not limited to, an electrode lead ("lead") with one or more electrodes disposed on a distal end of the lead and one or more terminals disposed on one or more proximal ends of the lead, Leads include, for example, deep brain stimulation leads, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,175,710; 8,224,450; 8,271,094; 8,295,944; 8,364,278; and 8,391,985; U.S. Patent Applications Publication Nos. 2007/0150036; 2009/0187222; 2009/0276021; 2010/0076535; 2010/0268298; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; and 2013/0105071; and U.S. patent application Ser. Nos. 12/177,823 and 13/750,725, all of which are incorporated by reference.

Figure 1:
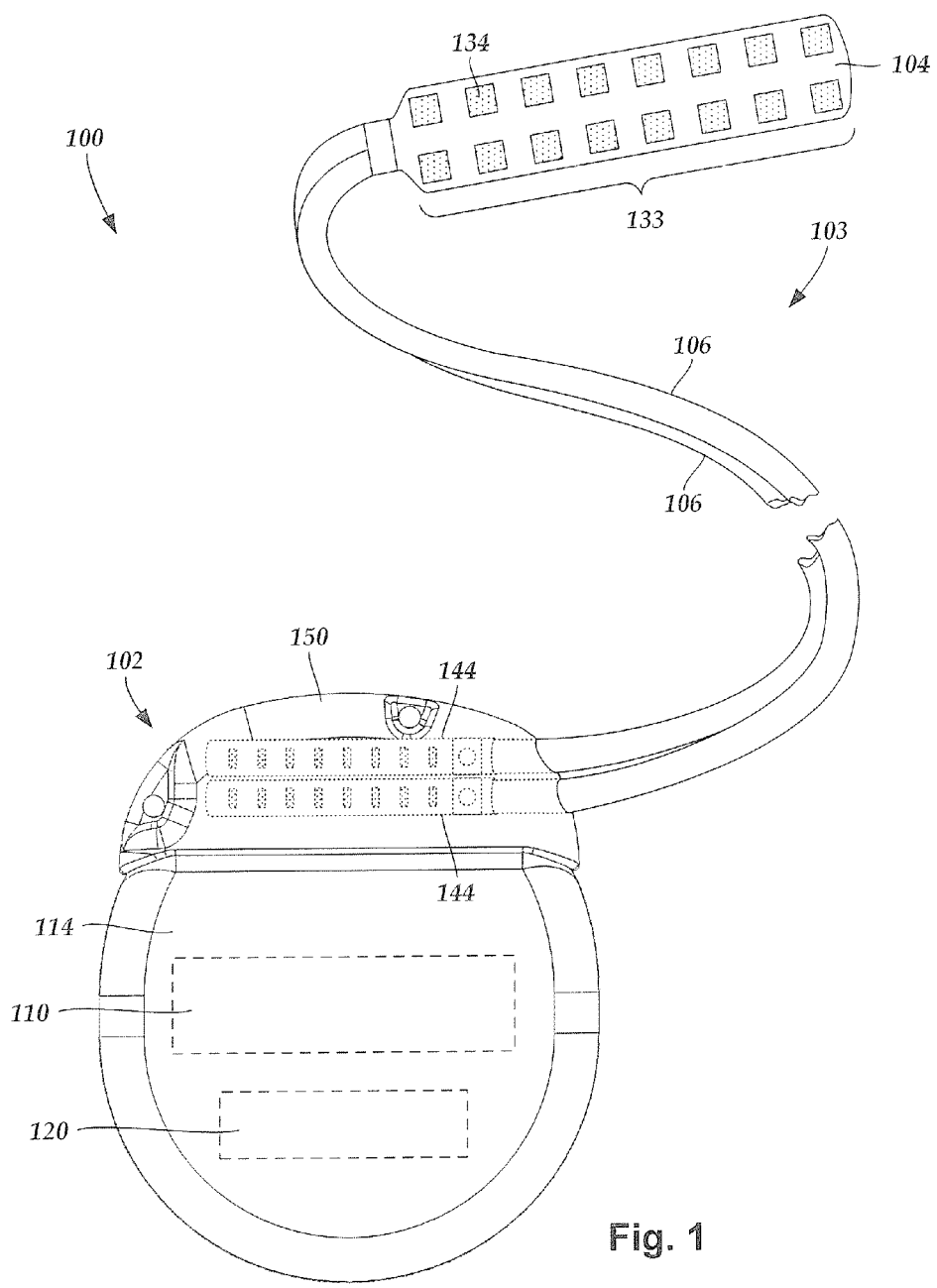
FIG. 1 is a schematic view of one embodiment of an implantable medical device that includes a paddle body coupled to a control module via lead bodies, according to the invention.

FIG. 1 illustrates schematically one embodiment of an electrical stimulation system 100. The electrical stimulation system includes a control module (e.g., a stimulator or pulse generator) 102 and a lead 103. The lead 103 including a paddle body 104 and one or more lead bodies 106 coupling the control module 102 to the paddle body 104. The paddle body 104 and the one or more lead bodies 106 form the lead 103. The paddle body 104 typically includes a plurality of electrodes 134 that form an array of electrodes 133. The control module 102 typically includes an electronic subassembly 110 and an optional power source 120 disposed in a sealed housing 114. In FIG. 1, two lead bodies 106 are shown coupled to the control module 102.

The control module 102 typically includes one or more connectors 144 into which the proximal end of the one or more lead bodies 106 can be plugged to make an electrical connection via connector contacts (e.g., 316 in FIG. 3A) disposed in the connector 144 and terminals (e.g., 310 in FIG. 3A) on each of the one or more lead bodies 106. The connector contacts are coupled to the electronic subassembly 110 and the terminals are coupled to the electrodes 134. In FIG. 1, two connectors 144 are shown.

The one or more connectors 144 may be disposed in a header 150. The header 150 provides a protective covering over the one or more connectors 144. The header 150 may be formed using any suitable process including, for example, casting, molding (including injection molding), and the like. In addition, one or more lead extensions 324 (see FIG. 3C) can be disposed between the one or more lead bodies 106 and the control module 102 to extend the distance between the one or more lead bodies 106 and the control module 102.

Figure 2:
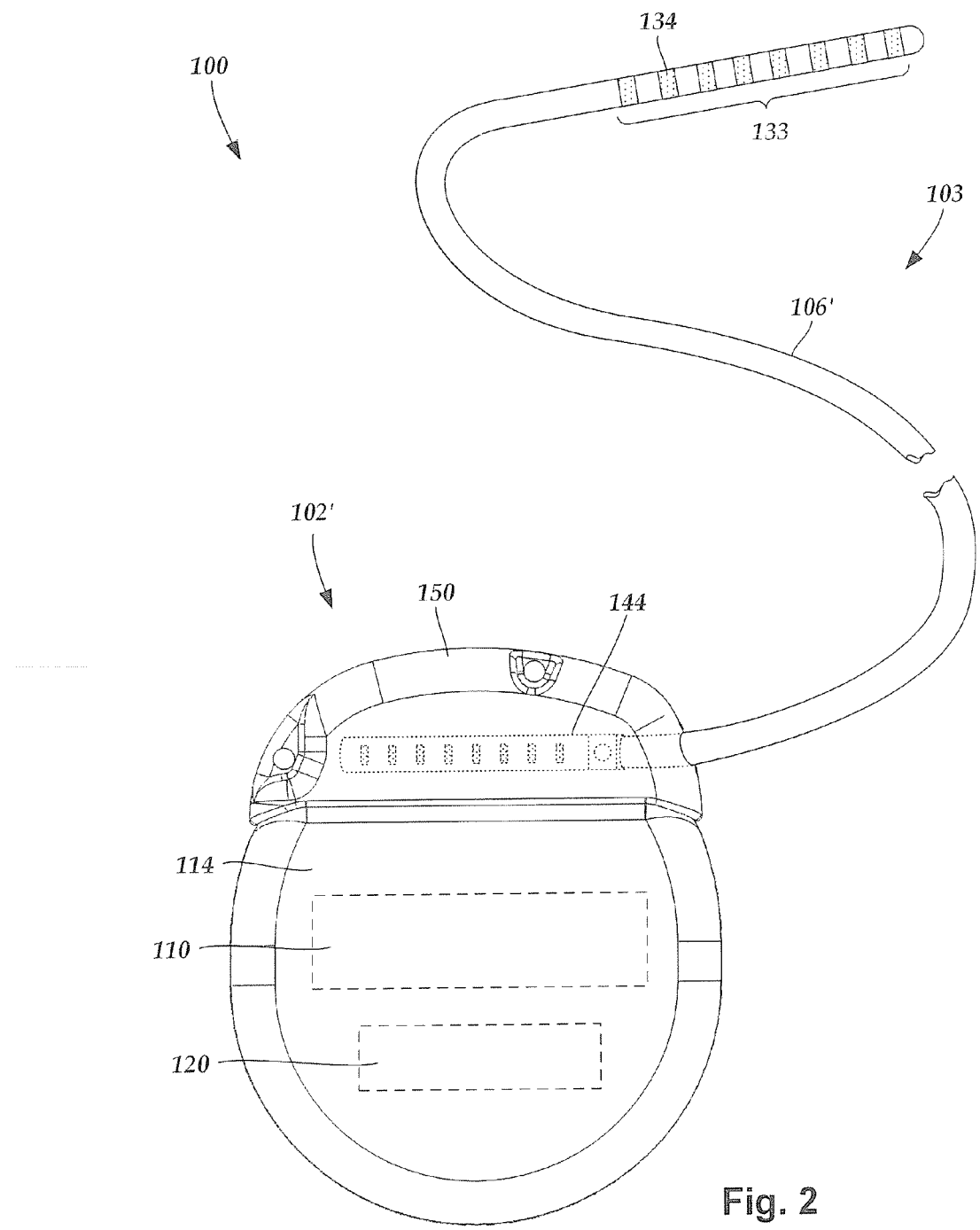
FIG. 2 is a schematic view of another embodiment of an implantable medical device that includes a percutaneous lead body coupled to a control module via a lead body, according to the invention.

It will be understood that the electrical stimulation system can include more, fewer, or different components and can have a variety of different configurations including those configurations disclosed in the electrical stimulation system references cited herein. For example, instead of a paddle body 104, the electrodes 134 can be disposed in an array at or near the distal end of a lead body 106' forming a percutaneous lead 103, as illustrated in FIG. 2. The percutaneous lead may be isodiametric along the length of the lead body 106". The lead body 106' can be coupled with a control module 102' with a single connector 144.

The electrical stimulation system or components of the electrical stimulation system, including one or more of the lead bodies 106, the control module 102, and, in the case of a paddle lead, the paddle body 104, are typically implanted into the body of a patient. The electrical stimulation system can be used for a variety of applications including, but not limited to, spinal cord stimulation, brain stimulation, neural stimulation, muscle activation via stimulation of nerves innervating muscle, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, titanium, or rhenium.

The number of electrodes 134 in the array of electrodes 133 may vary. For example, there can be two, three, four, five, six, seven, eight, nine, ten, eleven, twelve, thirteen, fourteen, fifteen, sixteen, or more electrodes 134. As will be recognized, other numbers of electrodes 134 may also be used. In FIG. 1, sixteen electrodes 134 are shown. The electrodes 134 can be formed in any suitable shape including, for example, round, oval, triangular, rectangular, pentagonal, hexagonal, heptagonal, octagonal, or the like.

The electrodes of the paddle body 104 or one or more lead bodies 106 are typically disposed in, or separated by, a non-conductive, biocompatible material including, for example, silicone, polyurethane, and the like or combinations thereof. The paddle body 104 and one or more lead bodies 106 may be formed in the desired shape by any process including, for example, molding (including injection molding), casting, and the like. Electrodes and connecting wires can be disposed onto or within a paddle body either prior to or subsequent to a molding or casting process. The non-conductive material typically extends from the distal end of the lead 103 to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Terminals (e.g., 310 in FIG. 3A) are typically disposed at the proximal end of the one or more lead bodies 106 for connection to corresponding conductive contacts (e.g., 316 in FIG. 3A) in connectors (e.g., 144 in FIG. 1) disposed on, for example, the control module 102 (or to other devices, such as conductive contacts on a lead extension, an operating room cable, a splitter, an adaptor, or the like).

Conductive wires (not shown) extend from the terminals (e.g., 310 in FIG. 3A) to the electrodes 134. Typically, one or more electrodes 134 are electrically coupled to a terminal (e.g., 310 in FIG. 3A). In some embodiments, each terminal (e.g., 310 in FIG. 3A) is only coupled to one electrode 134.

The conductive wires may be embedded in the non-conductive material of the lead or can be disposed in one or more lumens (not shown) extending along the lead. In some embodiments, there is an individual lumen for each conductive wire. In other embodiments, two or more conductive wires may extend through a lumen. There may also be one or more lumens (not shown) that open at, or near, the proximal end of the lead, for example, for inserting a stylet rod to facilitate placement of the lead within a body of a patient. Additionally, there may also be one or more lumens (not shown) that open at, or near, the distal end of the lead, for example, for infusion of drugs or medication into the site of implantation of the paddle body 104. The one or more lumens may, optionally, be flushed continually, or on a regular basis, with saline, epidural fluid, or the like. The one or more lumens can be permanently or removably sealable at the distal end.

As discussed above, the one or more lead bodies 106 may be coupled to the one or more connectors 144 disposed on the control module 102. The control module 102 can include any suitable number of connectors 144 including, for example, two three, four, five, six, seven, eight, or more connectors 144. It will be understood that other numbers of connectors 144 may be used instead. In FIG. 1, each of the two lead bodies 106 includes eight terminals that are shown coupled with eight conductive contacts disposed in a different one of two different connectors 144.

Figure 3A:
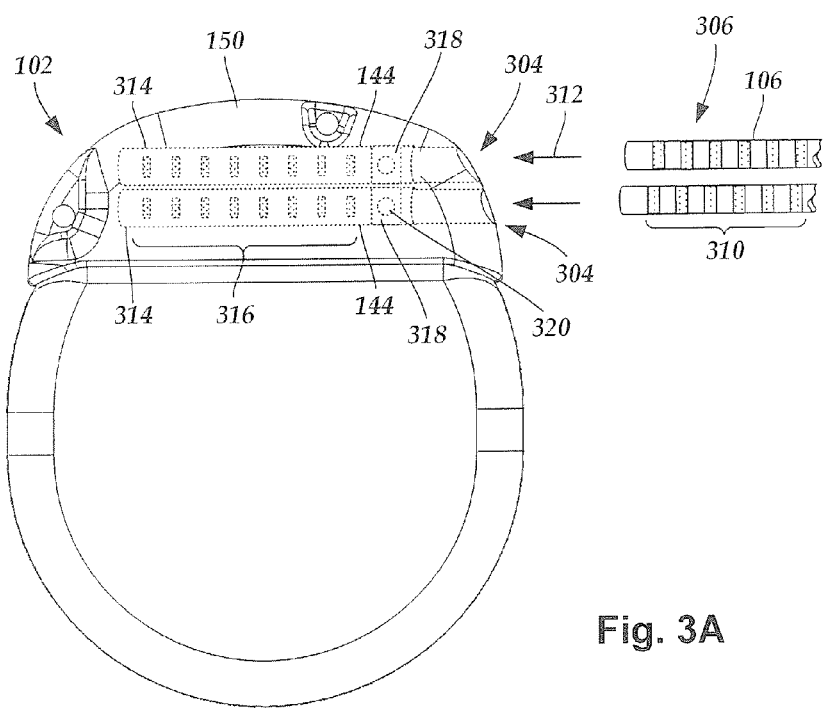
FIG. 3A is a schematic view of one embodiment of a plurality of connectors disposed in the control module of FIG. 1, the connectors configured and arranged to receive the proximal portions of the lead bodies of FIG. 1, according to the invention.
Figure 3B:
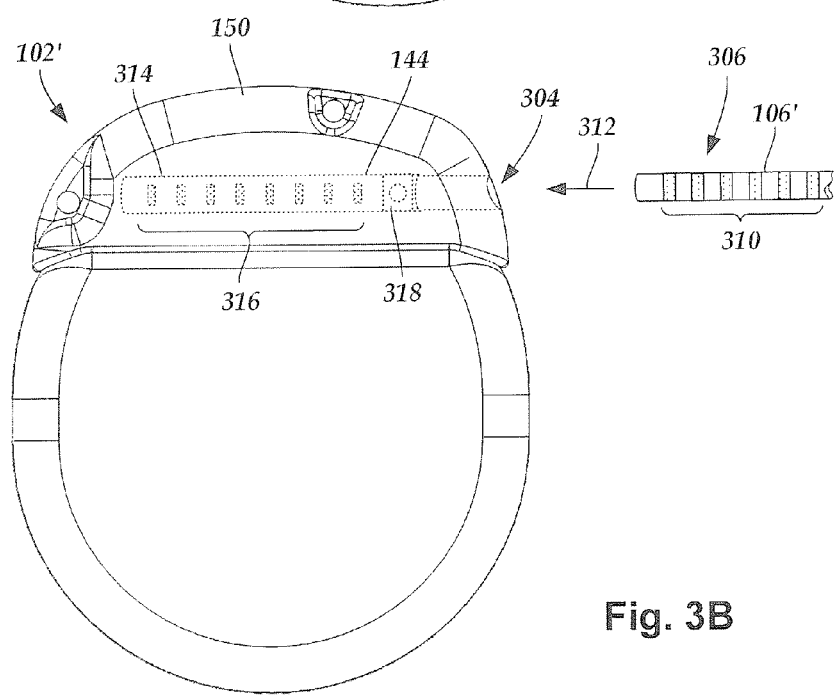
FIG. 3B is a schematic view of one embodiment of a connector disposed in the control module of FIG. 2, the connector configured and arranged to receive the proximal portion of one of the lead body of FIG. 2, according to the invention.

FIG. 3A is a schematic side view of one embodiment of a plurality of connectors 144 disposed on the control module 102. In at least some embodiments, the control module 102 includes two connectors 144. In at least some embodiments, the control module 102 includes four connectors 144. In FIG. 3A, proximal ends 306 of the plurality of lead bodies 106 are shown configured and arranged for insertion to the control module 102. FIG. 3B is a schematic side view of one embodiment of a single connector 144 disposed on the control module 102'. In FIG. 3B, the proximal end 306 of the single lead body 106' is shown configured and arranged for insertion to the control module 102'.

In FIGS. 3A and 3B, the one or more connectors 144 are disposed in the header 150. In at least some embodiments, the header 150 defines one or more lumens 304 into which the proximal end(s) 306 of the one or more lead bodies 106/106' with terminals 310 can be inserted, as shown by directional arrows 312, in order to gain access to the connector contacts disposed in the one or more connectors 144.

The one or more connectors 144 each include a connector housing 314 and a plurality of connector contacts 316 disposed therein. Typically, the connector housing 314 provides access to the plurality of connector contacts 316 via the lumen 304. In at least some embodiments, one or more of the connectors 144 further includes a retaining element 318 configured and arranged to fasten the corresponding lead body 106/106' to the connector 144 when the lead body 106/106' is inserted into the connector 144 to prevent undesired detachment of the lead body 106/106' from the connector 144. For example, the retaining element 318 may include an aperture 320 through which a fastener (e.g., a set screw, pin, or the like) may be inserted and secured against an inserted lead body 106/106'.

When the one or more lead bodies 106/106' are inserted into the one or more lumens 304, the connector contacts 316 can be aligned with the terminals 310 disposed on the one or more lead bodies 106/106' to electrically couple the control module 102 to the electrodes (134 of FIG. 1) disposed at a distal end of the one or more lead bodies 106. Examples of connectors in control modules are found in, for example, U.S. Pat. Nos. 7,244,150 and 8,224,450, which are incorporated by reference.

Figure 3C:
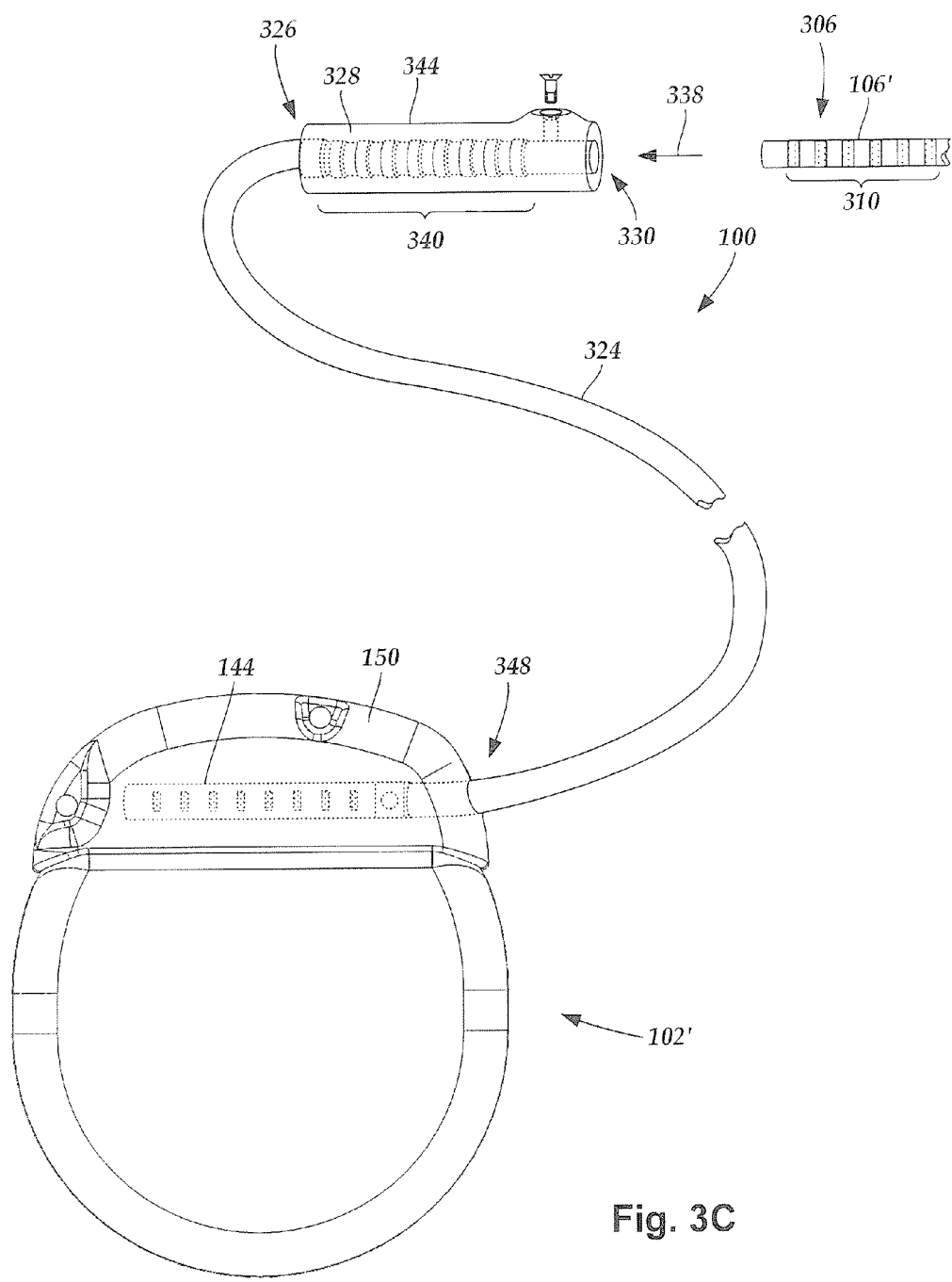
FIG. 3C is a schematic view of one embodiment of a proximal portion of the lead body of FIG. 2, a lead extension, and the control module of FIG. 2, the lead extension configured and arranged to couple the lead body to the control module, according to the invention.

In at least some embodiments, the electrical stimulation system includes one or more lead extensions. The one or more lead bodies 106/106' can be coupled to one or more lead extensions which, in turn, are coupled to the control module 102/102'. In FIG. 3C, a lead extension connector 322 is disposed on a lead extension 324. The lead extension connector 322 is shown disposed at a distal end 326 of the lead extension 324. The lead extension connector 322 includes a connector housing 344. The connector housing 344 defines at least one lumen 330 into which a proximal end 306 of the lead body 106' with terminals 310 can be inserted, as shown by directional arrow 338. The lead extension connector 322 also includes a plurality of connector contacts 340. When the lead body 106' is inserted into the lumen 330, the connector contacts 340 disposed in the connector housing 344 can be aligned with the terminals 310 on the lead body 106 to electrically couple the lead extension 324 to the electrodes (134 of FIG. 1) disposed at a distal end (not shown) of the lead body 106'.

The proximal end of a lead extension can be similarly configured and arranged as a proximal end of a lead body. The lead extension 324 may include a plurality of conductive wires (not shown) that electrically couple the connector contacts 340 to terminal on a proximal end 348 of the lead extension 324. The conductive wires disposed in the lead extension 324 can be electrically coupled to a plurality of terminals (not shown) disposed on the proximal end 348 of the lead extension 324. In at least some embodiments, the proximal end 348 of the lead extension 324 is configured and arranged for insertion into a lead extension connector disposed in another lead extension. In other embodiments (as shown in FIG. 3C), the proximal end 348 of the lead extension 324 is configured and arranged for insertion into the connector 144 disposed on the control module 102'.

It will be understood that the control modules 102/102' can receive either lead bodies 106/106' or lead extensions 324. It will also be understood that the electrical stimulation system 100 can include a plurality of lead extensions 224. For example, each of the lead bodies 106 shown in FIGS. 1 and 3A can, alternatively, be coupled to a different lead extension 224 which, in turn, are each coupled to different ports of a two-port control module, such as the control module 102 of FIGS. 1 and 3A.

Figure 4:
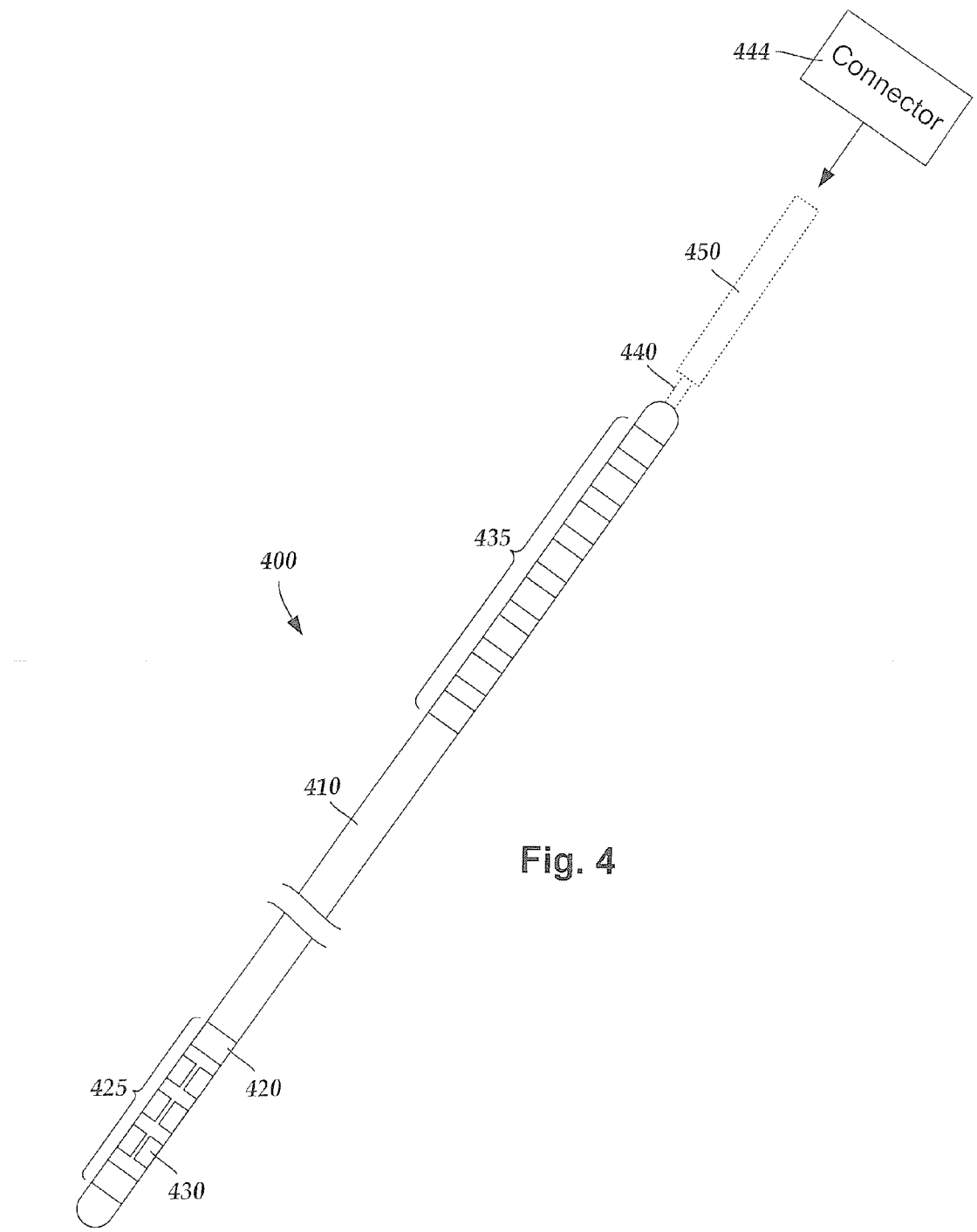
FIG. 4 is a schematic side view of yet another embodiment of an implantable medical device for brain stimulation, according to the invention.

Turning to FIG. 4, in the case of deep brain stimulation, the lead may include stimulation electrodes, recording electrodes, or a combination of both. At least some of the stimulation electrodes, recording electrodes, or both are provided in the form of segmented electrodes that extend only partially around the circumference of the lead. These segmented electrodes can be provided in sets of electrodes, with each set having electrodes circumferentially distributed about the lead at a particular longitudinal position.

In at least some embodiments, a practitioner may determine the position of the target neurons using recording electrode(s) and then position the stimulation electrode(s) accordingly. In some embodiments, the same electrodes can be used for both recording and stimulation. In some embodiments, separate leads can be used; one with recording electrodes which identify target neurons, and a second lead with stimulation electrodes that replaces the first after target neuron identification. In some embodiments, the same lead may include both recording electrodes and stimulation electrodes or electrodes may be used for both recording and stimulation.

FIG. 4 illustrates one embodiment of a device 400 for brain stimulation. The device includes a lead 410, a plurality of electrodes 425 disposed at least partially about a circumference of the lead 410, a plurality of terminals 435, a connector 444 for connection of the electrodes to a control unit, and a stylet 440 for assisting in insertion and positioning of the lead in the patient's brain. The stylet 440 can be made of a rigid material. Examples of suitable materials for the stylet include, but are not limited to, tungsten, stainless steel, and plastic. The stylet 440 may have a handle 450 to assist insertion into the lead 410, as well as rotation of the stylet 440 and lead 410. The connector 444 fits over a proximal end of the lead 410, preferably after removal of the stylet 440.

In FIG. 4, the electrodes 425 are shown as including both ring electrodes, such as ring electrode 420, and segmented electrodes, such as segmented electrodes 430. In some embodiments, the electrodes 425 are all segmented. In other embodiments, the electrodes 425 are all ring-shaped. In FIG. 4, each of the terminals 435 is shown as being ring-shaped.

The segmented electrodes of FIG. 4 are shown in sets of two, where the two segmented electrodes of a particular set are electrically isolated from one another and are circumferentially-offset along the lead 410. Any suitable number of segmented electrodes can be formed into a set including, for example, two, three, four, or more segmented electrodes.

Figure 5:
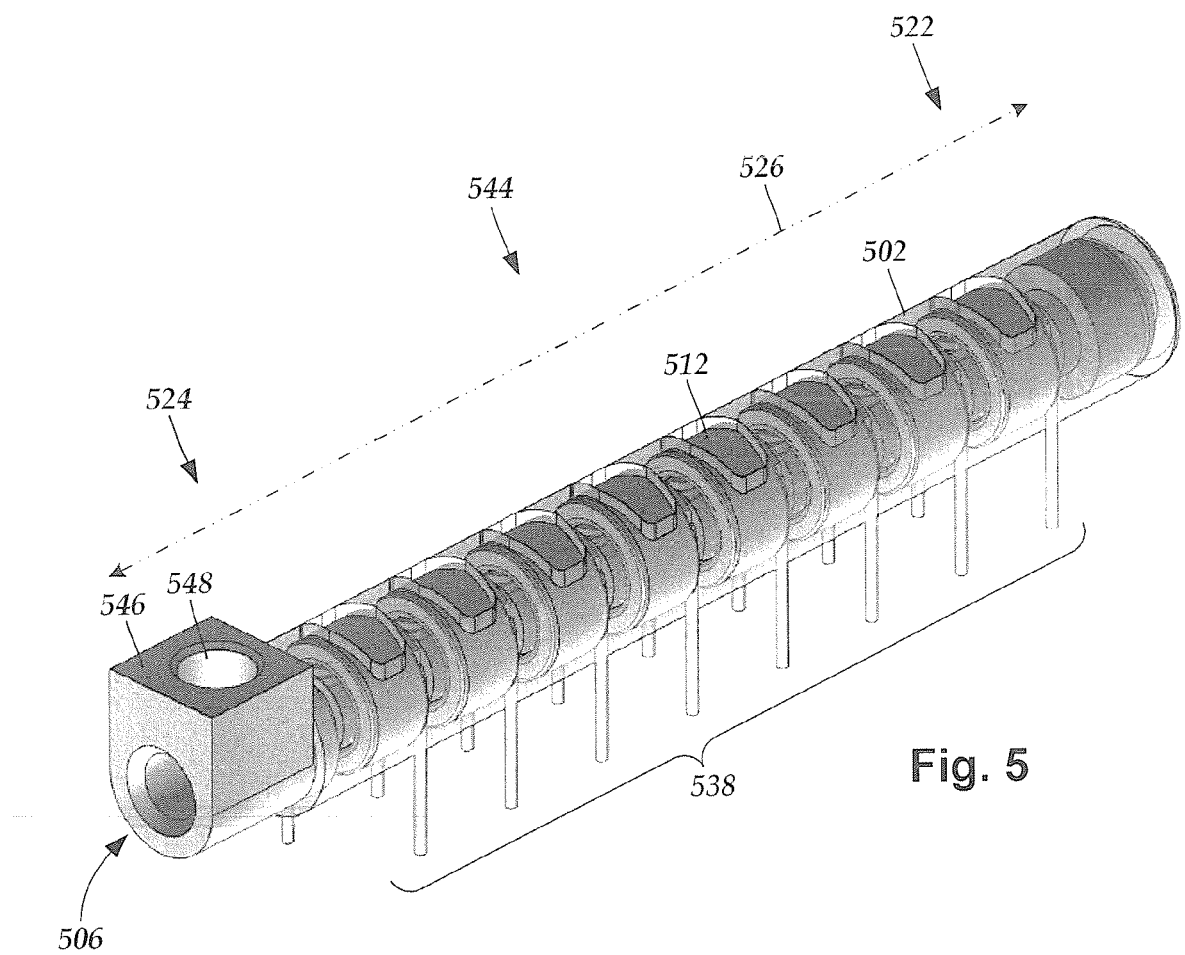
FIG. 5 is a schematic perspective view of one embodiment of a connector suitable for use with any of the implantable medical devices of FIGS. 1, 2, 3C, and 4, according to the invention.

Turning to FIG. 5, connector contacts (see e.g., 316 in FIGS. 3A-3B; and 340 in FIG. 3C) of electrical stimulation systems can be disposed in various types of connectors (see e.g., 144 in FIGS. 1-3C; 344 in FIG. 3C; and 444 in FIG. 4) that, in turn, are disposed along various types of implantable medical devices including, for example, control modules, lead extensions, adaptors, splitters, or the like. At least some conventional connectors use connector contacts formed from coiled springs adapted to completely encircle terminals of inserted elongated members (e.g., leads, lead extensions, or the like) when making electrical connection with those terminals. Such connector contacts can be labor-intensive and expensive to form and to dispose in connectors. Additionally, such connector contacts are bulky. The connector contacts are coiled and typically extend around an entire circumference of the connector within which the connector contacts are disposed. Consequently, it would be advantageous to utilize connectors with connector contacts that are cheaper to manufacture and less bulky, while continuing to provide a robust electrical connection between the connector contacts and inserted terminals of elongated members.

As herein described, an improved connector may be used with implantable medical devices, such as electrical stimulation systems. The improved connector includes connector contacts with biasing structures that are biased to maintain electrical contact with terminals of received elongated members. In at least some embodiments, the biasing structures include multiple biasing members. The connector contacts may, optionally, be formed from tubing.

The connector contacts are disposed in contact housings that are arranged along the connector and open to a connector lumen suitable for receiving an elongated member. The connector contacts are grouped into sets within the contact housings with the individual connector contacts of the sets being circumferentially-offset from one another along the contact housing such that the connector contacts are not electrically coupled to one another. In other words, the connector contacts include sets of segmented connector contacts.

It may be advantageous to design the connector with multiple sets of circumferentially-offset connector contacts (i.e., segmented connector contacts). Such a design may increase the number of connector contacts disposed in a connector from conventional connectors. For example, in at least some embodiments the design may enable a lead with electrodes disposed along two distal portions (e.g., for bilateral deep brain stimulation) to couple with a single connector.

In at least some embodiments, the design of the disclosed connector may enable the size of the connector to be decreased from conventional connectors. In at least some embodiments, the design may enable the number of connector contacts disposed in the connector to be increased without increasing the size of the connector. Such a design may also enable the connector to be compatible with elongated members having terminals that are either ring-shaped or segmented.

In at least some embodiments, when an elongated member with segmented terminals is received by the disclosed connector, the elongated member can be rotated relative to the connector such that each of the segmented terminals of a particular set of segmented terminals can be coupled to a different connector contact of a set of connector contacts within a contact housing. In at least some embodiments, when the inserted elongated member has ring-shaped terminals, the connector contacts of a particular set of connector contacts can be programmed (e.g., via the electronic subassembly 110) to operate as a single connector contact, or one or more of the connector contacts of the set of connector contacts can be shut off to prevent short-circuiting.

FIG. 5 illustrates, in perspective view, one embodiment of a connector 544 suitable for use with an implantable medical device, such as an electrical stimulation system. The connector 544 can be disposed, for example, on a control module, lead extension, adaptor, splitter, or the like. The connector 544 has a first end 522, an opposing second end 524, and a longitudinal length, shown in FIG. 5 by a dashed and dotted line 526. The connector 544 includes an elongated connector housing 502 that defines a connector lumen 506 suitable for receiving a portion of an elongated member, such as a lead, lead extension, or the like. In FIG. 5, the connector lumen 506 is defined along the second end 524 of the connector 544 and extends along the longitudinal length 526 of the connector 544. The first end 522 of the connector 544 can be either open or closed.

Multiple connector-contact assemblies, such as connector-contact assembly 512, are disposed in a spaced-apart relationship along the longitudinal length 526 of the connector housing 502 such that the connector-contact assemblies 512 are exposed to the connector lumen 506 and also to an array of conductive members 538. When, for example, the connector 544 is disposed on a lead extension, the conductive members 538 may couple the connector-contact assembly 512 to lead extension terminals. When, for example, the connector 544 is disposed on a control module, the conductive members 538 may couple the connector-contact assembly 512 to the electronic subassembly (110 in FIG. 1). In at least some embodiments, the conductive members 538 couple the connector-contact assembly 512 to the electronic subassembly (110 in FIG. 1) via feedthrough pins extending through the sealed housing (114 in FIG. 1)

Optionally, a retention block 546 is disposed along the connector 544. The retention block 546 can be used to facilitate retention of an elongated member (see e.g., 1203 in FIG. 13) when the elongated member is inserted into the connector lumen 506. In at least some embodiments, the retention block 546 defines a fastening aperture 548 configured to receive a fastener (e.g., a set screw, pin, or the like). In at least some embodiments, the fastener, when received by the fastener aperture 548, is configured to tighten against a portion of the elongated member (e.g., a retention sleeve) when the elongated member is inserted into the connector lumen 506.

Figure 6A:
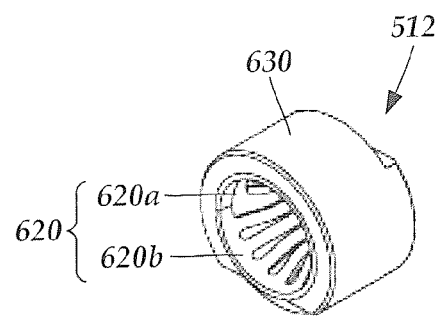
FIG. 6A is a schematic perspective view of one embodiment of a connector-contact assembly suitable for use with the connector of FIG. 5, the connector-contact assembly including a set of contact connectors disposed in a contact housing, according to the invention.
Figure 6B:
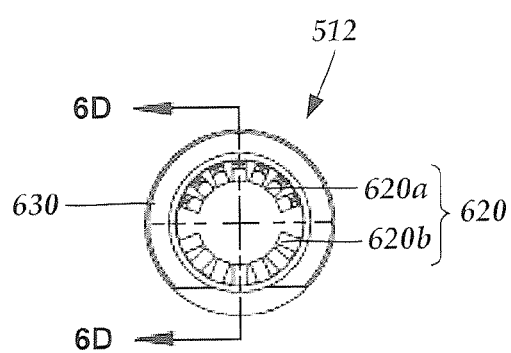
FIG. 6B is a schematic end view of one embodiment of the connector-contact assembly of FIG. 6A, according to the invention.
Figure 6C:
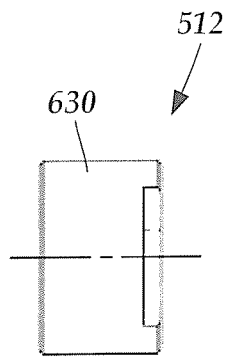
FIG. 6C is a schematic side view of one embodiment of the connector-contact assembly of FIG. 6A, according to the invention.
Figure 6D:
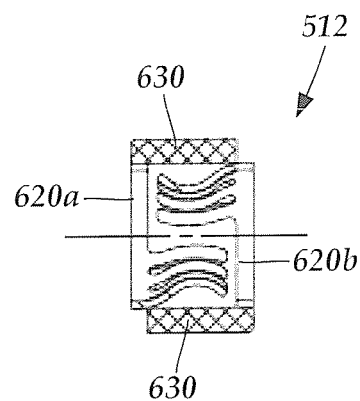
FIG. 6D is a schematic longitudinal cross-sectional view of one embodiment of the connector-contact assembly of FIG. 6A, according to the invention.

FIG. 6A illustrates, in perspective view, one embodiment of one of the connector-contact assemblies 512 shown in FIG. 5. FIG. 6B illustrates, in end view, one embodiment of the connector-contact assembly 512. FIG. 6C illustrates, in side view, one embodiment of the connector-contact assembly 512. FIG. 6D illustrates, in longitudinal cross-sectional view, one embodiment of the connector-contact assembly 512.

The connector-contact assemblies 512 each include a connector-contact set 620 disposed in a contact housing 630 such that the contact housing 630 covers at least a portion of each connector contact of the set of connector contacts 620. In at least some embodiments, the contact housing 630 is nonconductive. The connector-contact set 620 can include any suitable number of connector contacts including, for example, two, three, four, or more connector contacts. In FIGS. 6A-6D and in other figures, the connector-contact set 620 is shown having exactly two connector contacts 620a and 620b.

The connector contacts of the connector-contact set 620 are not in electrical contact with one another. In at least some embodiments, the connector contacts of the connector-contact sets are circumferentially offset from one another. In at least some embodiments, the connector contacts of the connector-contact set 620 are longitudinally-even with one another along the longitudinal length (526 in FIG. 5) of the connector (544 in FIG. 5). In other words, in at least some embodiments the connector contacts of the connector-contact set 620 are circumferentially distributed about the connector housing 630 at a particular longitudinal position of the connector.

The connector-contact set 620 can remain disposed in the contact housing in any suitable manner including, for example, an interference fit, adhesive, or the like or combinations thereof. In at least some embodiments, the connector-contact set 620 remains disposed in the contact housing solely by an interference fit.

Figure 7A:
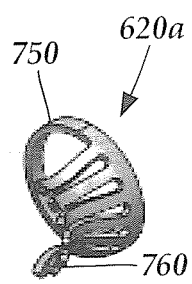
FIG. 7A is a schematic perspective view of one embodiment of a first connector contact suitable for use with the connector-contact assembly of FIG. 6A, according to the invention.
Figure 7B:
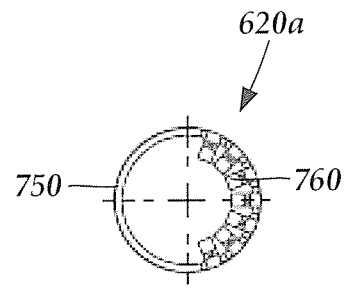
FIG. 7B is a schematic end view of one embodiment of the first connector contact of FIG. 7A, according to the invention.
Figure 7C:
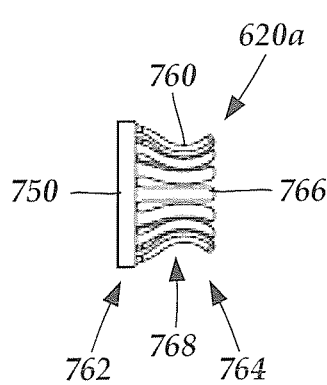
FIG. 7C is a schematic side view of one embodiment of the first connector contact of FIG. 7A, according to the invention.

FIG. 7A illustrates, in perspective view, one embodiment of the connector contact 620a of the connector-contact 620. FIG. 7B illustrates, in end view, one embodiment of the connector contact 620a. FIG. 7C illustrates, in side view, one embodiment of the connector contact 620a. The connector contacts, such as connector contact 620a, can be formed from any electrically-conductive material suitable for implantation including, for example, one or more shape-memory materials. MP35N, stainless steel, or the like or combinations thereof.

The connector contacts use biasing structures to create and maintain electrical contact with terminals of an inserted elongated member. In at least some embodiments, terminals of an inserted elongated member (e.g., 1203 of FIG. 12) couple to the connector contacts solely via the biasing structures of the connector contacts. The connector contacts may include any suitable number of biasing structures. In at least some embodiments, the connector contacts include a single biasing structure.

The biasing structures may be biased radially-inward. In which case, when the biasing structures are expanded radially outward when receiving the elongated member, the biasing of the biasing structures maintains physical contact with the received elongated member. The biasing structures may take any suitable form suitable for making electrical contact with an inserted elongated member. In at least some embodiments, the biasing structures include biasing members formed as elongated strips of conductive, biased material. In at least some embodiments, the biasing members are formed as elongated strips of conductive, biased material that extend in a direction that is parallel to a longitudinal length of the elongated member. In at least some embodiments, the biasing members are formed as elongated strips of conductive, biased material that extend in a direction that is parallel to the longitudinal length (526 in FIG. 5) of the connector (544 in FIG. 5).

In at least some embodiments, the biasing structures are attached to bases. In FIGS. 7A-7C and in other figures, the connector contact 620a includes a base 750 and a biasing structure, such as biasing structure 760, attached to the base 750. The biasing structures can include any suitable number of biasing members including, for example, two, three, four, five, six, seven, eight, nine, ten, or more biasing members. In at least some embodiments, the biasing structures include at least two biasing members. In at least some embodiments, the biasing structures include no more than ten biasing members. In at least some embodiments, the biasing structures include no less than two and no more than ten biasing members. In FIGS. 7A-7C, the biasing structure 760 is shown having seven biasing members.

In at least some embodiments, the biasing structures each include a proximal portion 762 attached to the base, an opposing distal portion 764 spaced away from the base, a distal tip 766 disposed along the distal portion 764, and one or more bends 768 disposed between the base and the distal tip 766.

The base can be any suitable shape having an outer surface suitable for disposing along an inner surface of the contact housing, and an inner surface suitable for receiving the elongated member (e.g., 1203 of FIG. 12). In at least some embodiments, the base is ring-shaped. In some embodiments, the base 750 forms a closed-loop of material. In other embodiments, the base forms an open-loop of material, or is C-shaped. In some embodiments, the base 750 extends along no less than 50%, 60%, 70%, 80%, 90%, or more of the entire perimeter of the inner surface (934 in FIGS. 9A-9C) of the contact housing 630 within which the connector contact is disposed. In some embodiments, the entire base is conductive. In other embodiments, only the portion of the base attached to the biasing structure is conductive.

The biasing structures extend along less than an entire perimeter of the inner surface (934 in FIGS. 9A-9C) of the contact housing 630 within which the connector contact is disposed. In some embodiments, the biasing structures extend along no more than 80%, 70%, 60%, 50%, 40%, 30%, 20%, or 10% of the entire perimeter of the inner surface (934 in FIGS. 9A-9C) of the contact housing 630 within which the connector contact is disposed. In at least some embodiments, the biasing structures extend along less than an entire perimeter of the base to which the biasing structure is attached. In some embodiments, the biasing structure extends along no more than 80%, 70%, 60%, 50%, 40%, 30%, 20%, or 10% of the entire perimeter of the base to which the biasing structure is attached.

The one or more bends 768 of the biasing structure narrows the bore of the open center portion (970 in FIGS. 9A-9C) to a diameter that is slightly less than a diameter of the elongated member insertable into the connector lumen (506 in FIG. 5). Thus, when the elongated member is inserted into the open center portion (970 in FIGS. 9A-9C) and through the base, portions of the inserted elongated member contact the one or more bends 668 of the biasing structure and longitudinally expands the narrowed portion of the bore of the connector-contact lumen at the one or more bends 668. The biasing of the biasing structure facilitates the biasing structure maintaining physical contact with the inserted elongated member along the bends 668.

Figure 8A:
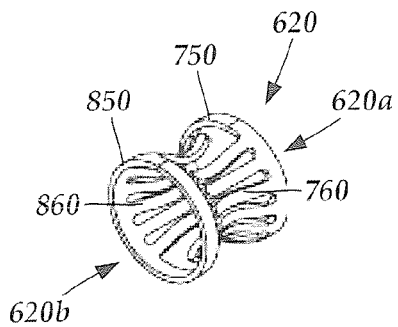
FIG. 8A is a schematic perspective view of one embodiment of a connector-contact set suitable for use with the connector-contact assembly of FIG. 6A, according to the invention.
Figure 8B:
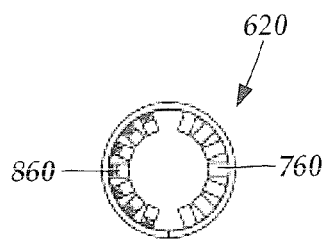
FIG. 8B is a schematic end view of one embodiment of the connector-contact set of FIG. 8A, according to the invention.
Figure 8C:
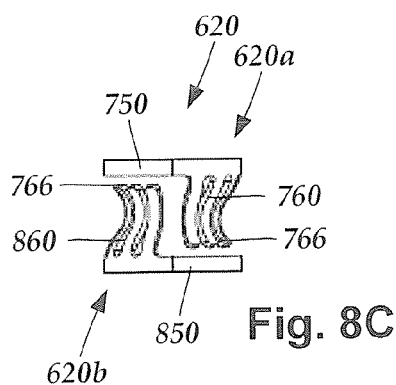
FIG. 8C is a schematic side view of one embodiment of the connector-contact set of FIG. 8A, according to the invention.

FIG. 8A illustrates, in perspective view, one embodiment of the connector-contact set 620. FIG. 8B illustrates, in end view, one embodiment of the connector-contact set 620. FIG. 8C illustrates, in side view, one embodiment of the connector-contact set 620. The connector-contact set 620 includes connector contact 620a and the connector contact 620b. The connector contact 620a includes the base 750 and biasing structure 760 attached to the base 750. Similarly, the connector contact 620b includes a base 850 and biasing structure 860 attached to the base 850.

In FIGS. 8A-8C, the connector contacts 620a and 620b each include closed-loop bases with biasing structures extending along less than 50% of the circumferences of the respective bases. The connector contacts 620a and 620b are arranged to form a generally cylindrical shape with the connector contact 620b flipped and rotated 180° relative to the connector contact 620a such that the bases 750, 850 form opposing ends of the generally cylindrical shape of the connector-contact set 620 and the biasing structures 760, 860 form circumferentially-offset partial side walls of the connector-contact set 620. In at least some embodiments, the biasing structures 760, 860 are circumferentially-opposite (e.g., 180° offset) from one another.

Figure 9A:
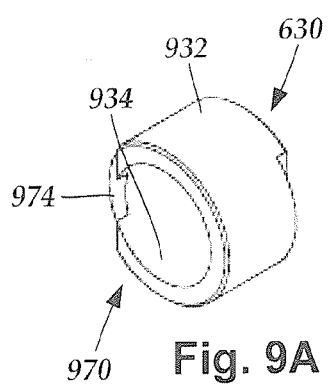
FIG. 9A is a schematic perspective view of one embodiment of a contact housing suitable for use with the connector-contact assembly of FIG. 6A, according to the invention.
Figure 9B:
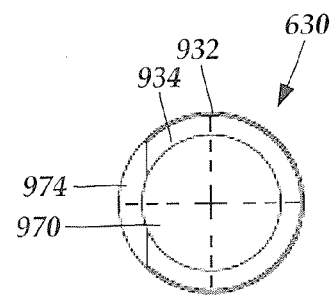
FIG. 9B is a schematic end view of one embodiment of the contact housing of FIG. 9A, according to the invention.
Figure 9C:
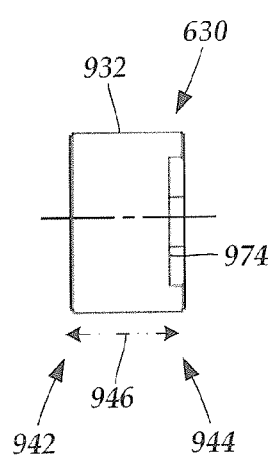
FIG. 9C is a schematic side view of one embodiment of the contact housing of FIG. 9A, according to the invention.

FIG. 9A illustrates, in perspective view, one embodiment of the contact housing 630 of the connector-contact assembly 512. FIG. 9B illustrates, in end view, one embodiment of the contact housing 630. FIG. 9C illustrates, in side view, one embodiment of the contact housing 630. The contact housings 630 can be formed in any shape suitable for receiving a connector-contact set, such as the connector-contact set 620, and also suitable for being disposed in a connector, such as the connector 544 of FIG. 5. In at least some embodiments, the contact housing 630 is nonconductive.

The contact housing 630 is shown in each of FIGS. 9A-9C as being cylindrical, or substantially cylindrical, and defining an outer surface 932 and an inner surface 934. The contact housing 630 has a first end 942, an opposing second end 944, and a longitudinal length, shown in FIG. 9C as a dashed and dotted line 946.

The inner surface 934 forms a perimeter of an open center portion 970 defined by the contact housing 630. The open center portion 970 is suitable for receiving the connector-contact set 620 with the connector contacts of the connector-contact set 620 arranged along the inner surface 934 of the contact housing 630 such that the connector contacts are circumferentially-offset from one another along the inner surface 934 and are not electrically coupled with one another. In at least some embodiments, the open center portion 970 is suitable for receiving a single connector-contact set 620. In at least some embodiments, the open center portion 970 receives the connector-contact set such that outer surfaces of the connector contacts of the received connector-contact set directly abut the inner surface 934 of the contact housing 630.

In at least some embodiments, the connector-contact set 620 is disposed in the open center portion 970 such that the base 750 of the connector contact 620a is disposed along the first end 642 of the contact housing 630 with the biasing members 760 extending towards the second end 644 of the contact housing 630. In at least some embodiments the connector-contact set 620 is disposed in the open center portion 970 such that the base 850 of the connector contact 620b is disposed along the second end 644 of the contact housing 630 with the biasing members 860 extending towards the first end 642 of the contact housing 630.

In at least some embodiments, the base 750 is flush with the first end 642 of the contact housing 630. Similarly, in at least some embodiments, the base 850 is flush with the second end 644 of the contact housing 630. In at least some embodiments, the connector-contact set 620 has a length that is equal to the longitudinal length 946 of contact housing 630.

FIG. 10A illustrates, in perspective view, one embodiment of the contact housing 630 and the connector-contact set 620. The connector-contact set 620 is configured and arranged for insertion into the open center portion 970 of the contact housing 630. FIG. 10B illustrates, in schematic perspective view, one embodiment of the connector-contact set 620 disposed in the open center portion 970 of the contact housing 630 to form the connector-contact assembly 512. In FIG. 10B, and in other figures, the bases of the connector contacts are shown as being flush with the ends 642, 644 of the contact housing 630.

Turning briefly back to FIGS. 9A-9C, in at least some embodiments one or more connection regions 974 are defined along the contact housing 630. The one or more connection regions 974 facilitate coupling of one or more conductive members (538 in FIG. 5) to each of the connector contacts of the connector-contact set. The connection region 974 may take any suitable form for facilitating making an electrical connection between the connector contacts and the one or more conductive members (538 in FIG. 5).

In at least some embodiments, the one or more connection regions 974 extend entirely through the contact housing 630 from the outer surface 932 to the inner surface 934. In at least some embodiments, at least one of the one or more connection regions 974 extends through the contact housing 630 along one of the ends 942, 944 of the contact housing 630. In at least some embodiments, at least one of the one or more connection regions 974 is formed as a notch, or cutout. In at least some embodiments, at least one of the one or more connection regions 974 is formed as an aperture defined along the longitudinal length 946 of the contact housing 630 that exposes a portion of at least one of the connector contacts along a side wall of the contact housing 630.

In FIGS. 9A-9C, and in other figures, a separate connection region 974 is shown for each connection between a conductive member (538 in FIG. 5) and one of the connector contacts of the connector-contact set. Additionally, in FIGS. 9A-9C, and in other figures, the connection regions 974 are shown as notches defined along opposing ends 942, 944 of the contact housing 630. In at least some embodiments, the connection regions 974 are circumferentially-offset from one another along the inner surface 934 of the contact housing 603. In at least some embodiments, the connection regions 974 are disposed along opposing ends 942, 944 of the contact housing 630. In at least some embodiments, the connection regions 974 are circumferentially-offset from one another along the inner surface 934 of the contact housing 603 and are disposed along opposing ends 942, 944 of the contact housing 630.

In at least some embodiments, the connection regions 974 are positioned such that they are adjacent to conductive portions of the connector contacts. In at least some embodiments, the biasing structures 760, 860 and the bases 750, 850 are both electrically conductive. In which case, the connection regions 974 can be disposed at locations along the contact housing 630 that are in adjacent to any portion of the connector contacts. In at least some embodiments, the biasing structures 760, 860 and the portion of the bases 750, 850 attached to the biasing structures 760, 860 are conductive, while portions of the bases 750, 850 that are circumferentially-opposed to the biasing structures 760, 860 are nonconductive. In which case, the connection regions 974 are disposed at locations along the contact housing 630 that are in adjacent to the biasing structures 760, 860.

FIG. 11A illustrates, in perspective view, one embodiment of conductive members 538a and 538b of the array of conductive members (538 in FIG. 5) coupled to the connector contacts of the connector-contact assembly 512. FIG. 11B illustrates, in end view, one embodiment of the conductive members 538a and 538b coupled to the connector contacts of the connector-contact assembly 512. FIG. 11C illustrates, in side view, one embodiment of the conductive members 538a and 538b coupled to the connector contacts of the connector-contact assembly 512. FIG. 11D illustrates, in bottom view, one embodiment of the conductive members 538a and 538b coupled to the connector contacts of the connector-contact assembly 512.

In each of FIGS. 11A-11D, the conductive members 538a and 538b are shown coupled to their respective connector contacts along connection regions 974. The locations of the connection regions 974 are shown on opposing ends 942 and 944 of the contact housing 630 and also on circumferentially-opposing portions of the contact housing 630. This orientation corresponds to the orientation of the connector contacts within the connector-contact set (620 in FIGS. 8A-8C).

FIGS. 11A-11D also show the conductive members 538a and 538b coupled to the connectors along the bases 750, 850, respectively. FIGS. 11A-11D additionally show the conductive members 538a and 538b coupled to the connectors along portions of the bases 750, 850, respectively, that attach to the biasing structures 760, 860, respectively. It will be understood that the conductive members can couple to any suitable conductive portions of the connector contacts, including along the portions of the bases 750, 850 circumferentially-opposite to the biasing structures 760, 860.

Turning to FIG. 12, as mentioned above the connector is configured to receive an elongated member (e.g., a lead, lead extension, or the like). The connector-contact assemblies of the connector are configured to couple with terminals disposed along the elongated member when the elongated member is received by the connector. In at least some embodiments, the elongated member includes at least one ring-shaped terminal. In at least some embodiments, the elongated member includes at least one segmented terminal, where the terminal extends around less than an entire circumference of the elongated member. Examples of elongated members with segmented terminals can be found in, for example, U.S. Patent Application Ser. No. 62/077,784, filed on even date herewith, entitled "Systems and Methods for Making and Using Improved Contact Arrays for Electrical Stimulation Systems" (Attorney Docket No. BSNC-1-383.0) which is incorporated by reference.

FIG. 12 illustrates, in perspective view, one embodiment of a proximal portion of a lead 1203 suitable for insertion into the connector lumen (506 in FIG. 5) of the connector (544 in FIG. 5). An array of terminals 1235 is disposed along the lead 1203. The array of terminals 1235 is suitable for contacting the connector-contact sets 620 of the connector when the lead 1235 is received by the connector lumen of the connector. In at least some embodiments, at least one of the terminals of the array 1235 is segmented.

The terminal array 1235 includes multiple segmented-terminal sets, such as segmented-terminal set 1245 which, in turn, includes multiple segmented terminals, such as segmented terminals 1245a and 1245b. In at least some embodiments, the individual terminals of the segmented-terminal sets 1245 are longitudinally-even with one another along the longitudinal length of the lead 1203. In at least some embodiments, the number of terminals of the segmented-terminal set is equal to the number of connector contacts of the connector-contact sets. In at least some embodiments, the number of segmented-terminal sets is equal to the number of connector-contact sets.

In some embodiments, the terminal array 1235 is formed exclusively from segmented terminals. In other embodiments, the terminal array 1235 is formed exclusively from ring-shaped terminals that extend around the entire circumference of the lead 1203. In at least some embodiments, the terminal array 1235 includes a combination of one or more ring-shaped terminals and one or more segmented terminals.

Optionally, a retention sleeve 1252 is disposed along the proximal portion of the lead 1203. The retention sleeve 1252 is configured and arranged to facilitate retention of the lead by the connector when the lead is received in the connector lumen (506 in FIG. 5). The retention sleeve 1252 is formed from a material that is typically harder than the material of the lead body and is configured to be tightened between a fastener received by the fastener aperture (548 in FIG. 5) and a side wall of the connector lumen (506 in FIG. 5) or the inner surface (934 in FIGS. 9A-9C) of one of the contact housings (630 in FIGS. 6A-6D). The retention sleeve 1252 may be positioned at any suitable location along the lead including, for example, distal to the distal-most terminal of the terminal array 1235.

Optionally, the electrical stimulation system includes an alignment assembly 1260 to ensure that, when the lead includes one or more segmented-terminal sets, the terminals are circumferentially aligned with the connector contacts of the connector-contact sets. In other words, the alignment assembly facilitates circumferential alignment of the terminals of the one or more segmented-terminal sets relative to the biasing structures of the connector contacts of the connector-contact sets. Circumferentially-aligning the terminals with the connector contacts may serve to prevent undesired electrical connections (e.g., short-circuiting) between connector contacts and undesired terminals, or other connector contacts, or both.

In at least some embodiments, the alignment assembly includes one or more elements (e.g., circumferentially-alignable markers, matable elements, or the like) that are disposed along the proximal portion of the lead, or along a portion of the connector, or both, and that can be used to visually identify the circumferential orientation of the lead relative to the connector when the lead is being inserted into the connector.

Note that the circumferential orientation of the connector contacts relative to the connector can be known and can also be constant. In which case, the circumferential orientation of the connector contacts can be determined by viewing the circumferential orientation of the connector. In at least some embodiments, the connector block (546 in FIGS. 5 and 13) is a visually distinct element along the exterior of the connector that can be used as a circumferential marker.

In FIG. 12, and in other figures, the alignment assembly 1260 includes alignment members 1262 extending outwardly from circumferentially-opposed portions of the lead. The alignment members 1262 can be visually aligned relative to the retention block (546 in FIG. 5; see also FIG. 13).

In at least some embodiments, the alignment assembly includes two or more matable elements (e.g., one or more notches/grooves, tabs/slots, or the like), where one element of the matable elements is disposed along the lead, and the other element of the matable elements is disposed along the connector, and where the lead cannot be fully inserted into the connector unless the matable elements are aligned and mated. In at least some embodiments, the retention block (546 in FIGS. 5 and 13) includes one or more grooves, or slots, or the like, that are configured to only mate with the alignment members 1262 of the lead when the segmented terminals of the lead are oriented circumferentially with the connector contacts of the connector. The alignment assembly can include any suitable number of alignment members including, for example, one, two, three, four, five, six, seven, eight, or more alignment members.

The alignment assembly can be disposed along any suitable portions of the lead, connector, or both. For example, in at least some embodiments at least one of the alignment members is disposed distal to distal-most terminal of the terminal array 1235. At least one of the alignment members may also be disposed distal to the retention sleeve 1252. Additionally, or alternately, one or more alignment members may be disposed proximal to the distal-most terminal of the terminal array 1235. In at least some embodiments, at least one of the alignment members is disposed at the proximal tip of the lead, or proximal to the proximal-most terminal of the terminal array 1235. In at least some embodiments, at least a portion of the alignment assembly is disposed along the second end (524 in FIG. 5) of the connector 544. Additionally, or alternately, one or more portions of the alignment assembly may be disposed in the connector along any suitable portion of the connector lumen (506 in FIG. 5). For example, one or more grooves or channels may extend along the longitudinal length of the connector within the connector lumen and may be configured to mate with the alignment members of the lead.

Figure 13:
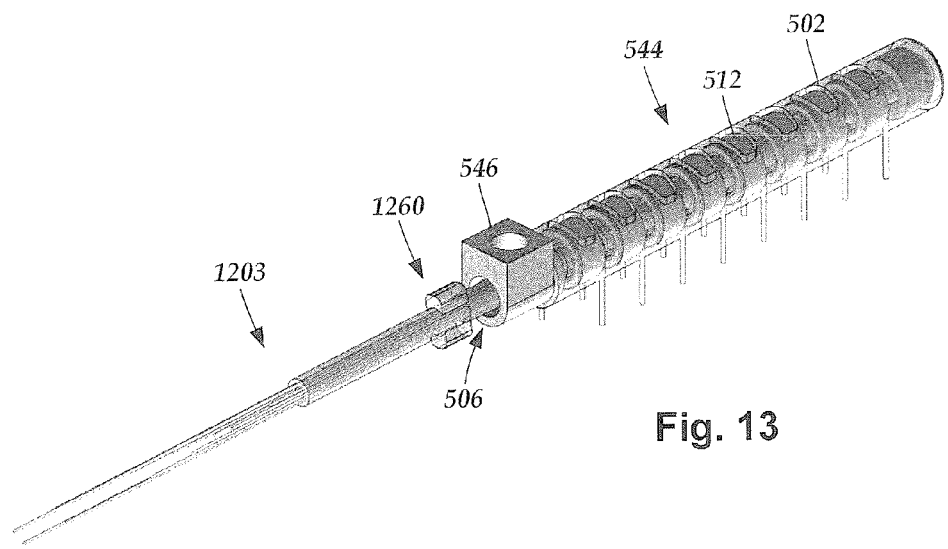
FIG. 13 is a schematic perspective view of one embodiment of a proximal portion of the lead of FIG. 12 disposed in the connector of FIG. 5, according to the invention.

Turning to FIG. 13, the lead 1203 is configured for insertion into the connector 544. FIG. 13 illustrates, in perspective view, one embodiment of a proximal portion of the lead 1203 disposed in the connector lumen 506 of the connector 544. In at least some embodiments, the alignment assembly 1260 is aligned with the retention block 546 for ensuring that the segmented terminals of the terminal array (1235 in FIG. 12) of the lead 1203 are circumferentially aligned with the biasing members of the connector-contact assemblies 512.

Figure 14A:
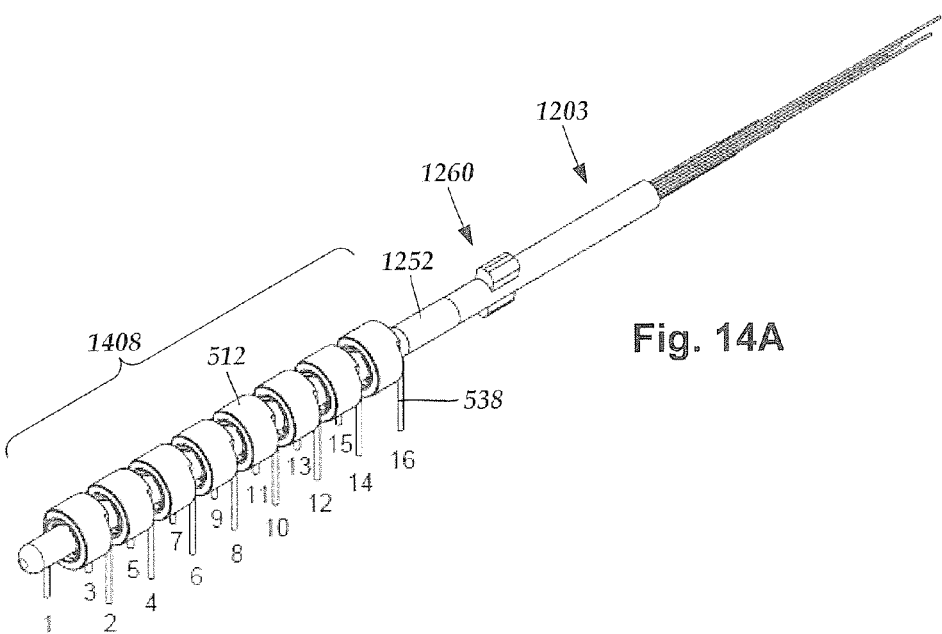
FIG. 14A is a schematic perspective view of one embodiment of terminals of the lead of FIG. 12 coupled to connector-contact assemblies of the connector of FIG. 5, according to the invention.
Figure 14B:
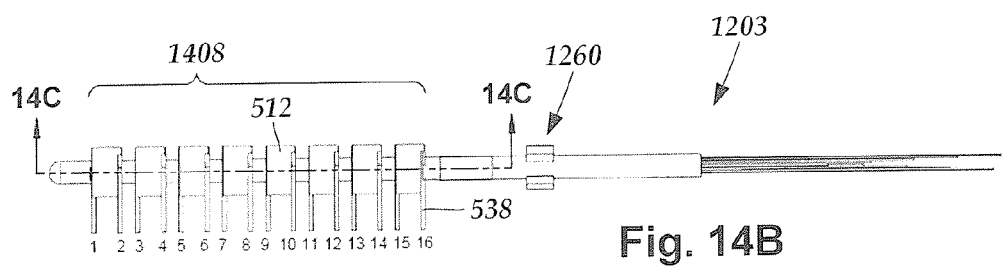
FIG. 14B is a schematic side view of one embodiment of terminals of the lead of FIG. 12 coupled to connector-contact assemblies of the connector of FIG. 5, according to the invention.
Figure 14C:
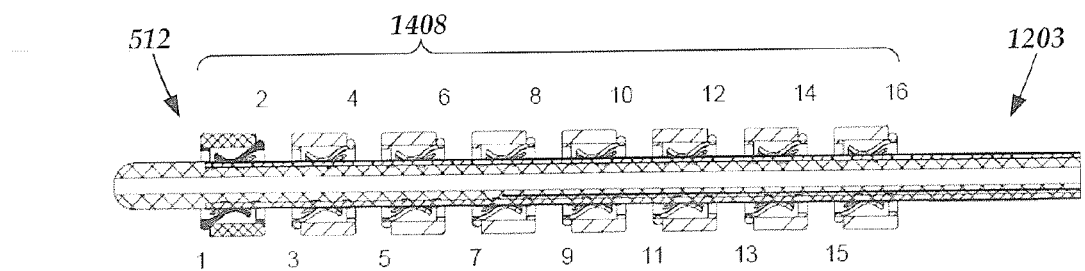
FIG. 14C is a schematic longitudinal cross-sectional view of one embodiment of terminals of the lead of FIG. 12 coupled to connector-contact assemblies of the connector of FIG. 5, according to the invention.

Turning to FIGS. 14A-14C, the connector-contact assemblies 512 are configured into a longitudinally-spaced-apart arrangement that facilitates making electrical contact with terminals disposed along inserted elongated members (e.g., leads, lead extensions, or the like). FIGS. 14A-14C show several different views of the lead 1203 disposed in the connector 544. In each of FIGS. 14A-14C, the connector housing 502 of the connector 544 is removed to more clearly show the connector-contact assemblies 512 of the connector 544.

FIG. 14A illustrates, in perspective view, one embodiment of terminals of the lead 1203 coupled to connector-contact assemblies 512 of the connector (544 in FIG. 13). FIG. 14B illustrates, in side view, one embodiment of terminals of the lead 1203 coupled to the connector-contact assemblies 512. FIG. 14C illustrates, in longitudinal cross-sectional view, one embodiment of terminals of the lead 1203 coupled to connector-contact assemblies 512.

FIGS. 14A-14C show multiple connector-contact assemblies, such as connector-contact assembly 512, arranged into an array 1408 of connector-contact assemblies 512 suitable for disposing in the connector 544. When, as shown in FIGS. 14A-14C, multiple connector-contact assemblies 512 are arranged along the connector, multiple longitudinally-spaced-apart portions of the connector lumen (506 in FIGS. 5 and 13) may be formed by the multiple connector-contact assemblies 512.

Figure 15:
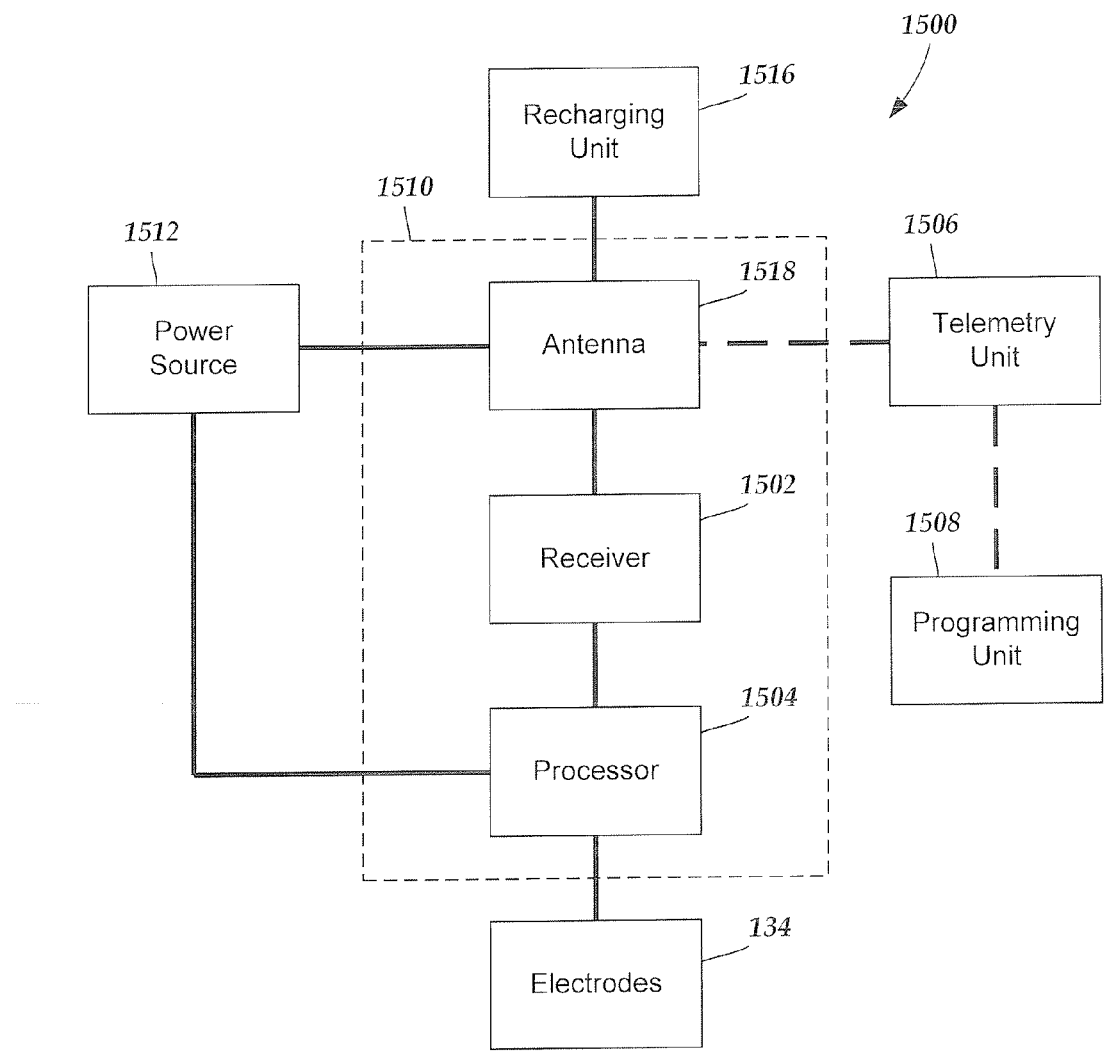
FIG. 15 is a schematic overview of one embodiment of components of an electrical stimulation system, according to the invention.

Turning to FIG. 15, the above-described connector-contact assemblies may be manufactured using any suitable technique. In at least some embodiments, the connector-contact assemblies are formed from tubing. It may be advantageous to form the connector-contact assemblies from tubing, rather than from flat sheets of material. Forming the connector-contact assemblies from tubing may be less expensive than forming the connector-contact assemblies from flat sheets of material.

Moreover, forming the connector-contact assemblies from tubing removes the seams that are inherent in techniques that involve forming the connector-contact assemblies from flat sheets of material. When flat sheets of metal are bent to form cylinders, a seam is formed along the opposing edges of the sheets of material that extend along the lengths of both the connector contact and the contact housing. The seam may prevent an interference fit from being formable between the connector contact and the contact housing. Examples of techniques for manufacturing connector-contact assemblies from tubing can be found in, for example, U.S. Provisional Patent Application Ser. No. 62/044,050 which is incorporated by reference.

FIG. 15 is a schematic overview of one embodiment of components of an electrical stimulation system 1500 including an electronic subassembly 1510 disposed within a control module. It will be understood that the electrical stimulation system can include more, fewer, or different components and can have a variety of different configurations including those configurations disclosed in the stimulator references cited herein.

Some of the components (for example, power source 1512, antenna 1518, receiver 1502, and processor 1504) of the electrical stimulation system can be positioned on one or more circuit boards or similar carriers within a sealed housing of an implantable pulse generator, if desired. Any power source 1512 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 1518 or a secondary antenna. The external power source can be in a device that is mounted on the skin of the user or in a unit that is provided near the user on a permanent or periodic basis.

If the power source 1512 is a rechargeable battery, the battery may be recharged using the optional antenna 1518, if desired. Power can be provided to the battery for recharging by inductively coupling the battery through the antenna to a recharging unit 1516 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 1504 is generally included to control the timing and electrical characteristics of the electrical stimulation system. For example, the processor 1504 can, if desired, control one or more of the timing, frequency, strength, duration, and waveform of the pulses. In addition, the processor 1504 can select which electrodes can be used to provide stimulation, if desired. In some embodiments, the processor 1504 may select which electrode(s) are cathodes and which electrode(s) are anodes. In some embodiments, the processor 1504 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1508 that, for example, allows modification of pulse characteristics. In the illustrated embodiment, the processor 1504 is coupled to a receiver 1502 which, in turn, is coupled to the optional antenna 1518. This allows the processor 1504 to receive instructions from an external source to, for example, direct the pulse characteristics and the selection of electrodes, if desired.

In one embodiment, the antenna 1518 is capable of receiving signals (e.g., RF signals) from an external telemetry unit 1506 which is programmed by a programming unit 1508. The programming unit 1508 can be external to, or part of, the telemetry unit 1506. The telemetry unit 1506 can be a device that is worn on the skin of the user or can be carried by the user and can have a form similar to a pager, cellular phone, or remote control, if desired. As another alternative, the telemetry unit 1506 may not be worn or carried by the user but may only be available at a home station or at a clinician's office. The programming unit 1508 can be any unit that can provide information to the telemetry unit 1506 for transmission to the electrical stimulation system 1500. The programming unit 1508 can be part of the telemetry unit 1506 or can provide signals or information to the telemetry unit 1506 via a wireless or wired connection. One example of a suitable programming unit is a computer operated by the user or clinician to send signals to the telemetry unit 1506.

The signals sent to the processor 1504 via the antenna 1518 and receiver 1502 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 1500 to cease operation, to start operation, to start charging the battery, or to stop charging the battery. In other embodiments, the stimulation system does not include an antenna 1518 or receiver 1502 and the processor 1504 operates as programmed.

Optionally, the electrical stimulation system 1500 may include a transmitter (not shown) coupled to the processor 1504 and the antenna 1518 for transmitting signals back to the telemetry unit 1506 or another unit capable of receiving the signals. For example, the electrical stimulation system 1500 may transmit signals indicating whether the electrical stimulation system 1500 is operating properly or not or indicating when the battery needs to be charged or the level of charge remaining in the battery. The processor 1504 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A connector for an implantable electrical medical device, the connector comprising:
   an elongated connector housing having a first end and an opposing second end;
   a connector lumen defined in the connector housing, the connector lumen configured and arranged to receive a lead or lead extension;
   a plurality of connector-contact assemblies disposed in the connector lumen, each of the plurality of connector-contact assemblies comprising
   a contact housing having a first end, an opposing second end, a longitudinal length, an inner surface, and an outer surface, the contact housing defining an open center portion with the inner surface of the contact housing forming a perimeter of the inner surface of the contact housing, the open center portion having an inner diameter, and a plurality of connector contacts arranged along the perimeter of the inner surface of the contact housing such that the plurality of connector contacts are not in electrical contact with one another, each of the plurality of connector contacts comprising a biasing structure configured and arranged to physically contact one of a plurality of terminals disposed along the lead or lead extension when the lead or lead extension is received by the connector lumen, for each of the plurality of connector contacts of the connector-contact assembly the biasing structure extends around no more than 70% of the perimeter of the inner surface of the contact housing and is circumferentially-offset from the biasing structures of the remaining connector contacts of the connector-contact assembly along the perimeter of the inner surface of the contact housing; and a plurality of connector conductors coupled to the plurality of connector-contact assemblies and extending along the connector housing.

2. The connector of claim 1, wherein each of the plurality of connector contacts comprises exactly one biasing structure.

3. The connector of claim 1, wherein the biasing structure comprises a plurality of biasing members.

4. The connector of claim 1, wherein the contact housing is electrically nonconductive.

5. The connector of claim 1 wherein, for each of the plurality of connector contacts, the biasing structure comprises at least one bend that extends into the open center portion of the contact housing and narrows the inner diameter of the open center portion.

6. The connector of claim 5 wherein, for each of the plurality of connector-contact assemblies, the plurality of connector contacts comprises a first connector contact having a first base and a second connector contact having a second base, and wherein the first connector contact and the second conductor contact are oriented in the contact housing with the first base disposed along the first end of the contact housing and the second base disposed along the second end of the contact housing.

7. The connector of claim 1 wherein, for each of the plurality of connector contacts, the connector contact comprises a base that is coupled to the biasing structure and that extends along at least 50% of the perimeter of the inner surface of the contact housing.

8. The connector of claim 1 wherein, for at least one of the plurality of connector-contact assemblies, the contact housing defines at least one connection region that extends through the contact housing from the outer surface to the inner surface and exposes a portion of at least one connector contact of the plurality of connector contacts disposed in the open center region of the contact housing to the outer surface of the contact housing.

9. The connector of claim 8 wherein, for at least one of the plurality of connector-contact assemblies, at least one of the plurality of connector contacts is aligned with the at least one connection region.

10. The connector of claim 8 wherein, for at least one of the plurality of connector-contact assemblies, the at least one connection region comprises a first connection region defined along the first end of the contact housing and a second connection region defined along the second end of the contact housing.

11. The connector of claim 10, wherein the first connection region and the second connection region are circumferentially-offset from one another along the perimeter of the inner surface of the contact housing.

12. The connector of claim 1 wherein, for at least one of the plurality of connector-contact assemblies, the connector-contact assembly comprises exactly two connector contacts.

13. A lead extension comprising:
a lead extension body with a proximal portion, a distal portion, a circumference, and a longitudinal length;
the connector of claim 1 disposed along the distal portion of the lead extension body;
a plurality of lead extension terminals disposed along the proximal portion of the lead extension body; and
a plurality of lead extension conductors electrically coupling the plurality of connector contacts of the connector to the plurality of lead extension terminals.

14. A lead assembly comprising:
the lead extension of claim 13; and
a lead configured and arranged for insertion into the connector lumen of the connector of the lead extension, the lead comprising
a lead body with a proximal portion, a distal portion, a circumference, and a longitudinal length,
a plurality of lead electrodes disposed along the distal portion of the lead body,
a plurality of lead terminals disposed along the proximal portion of the lead body, and
a plurality of lead conductors electrically coupling the plurality of lead electrodes to the plurality of lead terminals.

15. A kit for an electrical stimulation system comprising:
the lead extension of claim 13; and
a control module coupleable to the proximal portion of the lead extension, the control module comprising
a housing, and
an electronic subassembly disposed in the housing.

16. An electrical stimulation system comprising:
the kit of claim 15; and
a lead configured and arranged for insertion into the connector lumen of the connector of the control module of the kit, the lead comprising
a lead body with a proximal portion, a distal portion, a circumference, and a longitudinal length,
a plurality of lead electrodes disposed along the distal portion of the lead body,
a plurality of lead terminals disposed along the proximal portion of the lead body, and
a plurality of lead conductors electrically coupling the plurality of lead electrodes to the plurality of lead terminals.

17. A method of implanting an electrical stimulation system into a patient, the method comprising:
advancing the lead of the electrical stimulation system of claim 16 into the patient;
inserting the proximal portion of the lead body into the connector lumen of the connector of the lead extension of the electrical stimulation system; and
coupling the proximal portion of the lead extension body to the control module of the electrical stimulation system.

18. A control module comprising:
a sealed housing;
an electronic subassembly disposed in the sealed housing;
a header coupled to the sealed housing; and
the connector of claim 1 disposed in the header.

19. An electrical stimulation system comprising:
the control module of claim 18; and
a lead configured and arranged for insertion into the connector lumen of the connector of the control module, the lead comprising
 a lead body with a proximal portion, a distal portion, a circumference, and a longitudinal length,
 a plurality of lead electrodes disposed along the distal portion of the lead body,
 a plurality of lead terminals disposed along the proximal portion of the lead body, and
 a plurality of lead conductors electrically coupling the plurality of lead electrodes to the plurality of lead terminals.

20. A method of implanting an electrical stimulation system into a patient, the method comprising:
advancing the lead of the electrical stimulations system of claim 19 into the patient; and
inserting the proximal portion of the lead body into the connector lumen of the connector of the control module of the electrical stimulation system.

\* \* \* \* \*